United States Patent [19]

Rohde et al.

[11] Patent Number: 4,609,651
[45] Date of Patent: Sep. 2, 1986

[54] 11β-ARYLESTRADIENES, THEIR PRODUCTION, AND PHARMACEUTICAL PREPARATIONS CONTAINING SAME

[75] Inventors: Ralph Rohde, Berlin; Klaus Annen, Münster-Albachten; Gunter Neef, Berlin; Rudolf Wiechert, Berlin; Sybille Beier, Berlin; Walter Elger, Berlin; David Henderson, Berlin, all of Fed. Rep. of Germany

[73] Assignee: Schering Aktiengesellschaft, Berlin and Bergkamen, Fed. Rep. of Germany

[21] Appl. No.: 685,088

[22] Filed: Dec. 21, 1984

[30] Foreign Application Priority Data

Dec. 22, 1983 [DE] Fed. Rep. of Germany ....... 3347126

[51] Int. Cl.$^4$ .............................................. A61K 31/56
[52] U.S. Cl. ................................ 514/179; 260/397.45; 540/15; 540/36; 540/40; 540/47; 540/107; 540/108
[58] Field of Search .................. 260/397.45, 239.55 C; 514/179

[56] References Cited

U.S. PATENT DOCUMENTS 4,233,296 11/1980 Teutsch et al. .
4,457,925 7/1984 Bittler et al. .
4,477,445 10/1984 Philibert et al. ........... 260/239.55 R
4,519,946 5/1985 Teutsch et al. ................ 260/397.45
4,536,401 8/1985 Neef et al. ..................... 260/397.45

OTHER PUBLICATIONS

Belanger, A., et al. "Regio and Stereospecific Synthesis of 11-Substituted 19-Steroids", Steroids, vol. 37, No. 4, pp. 361-382, 4/81.

Primary Examiner—Elbert L. Roberts
Attorney, Agent, or Firm—Millen & White

[57] ABSTRACT

11β-Arylestradienes of general Formula I are disclosed

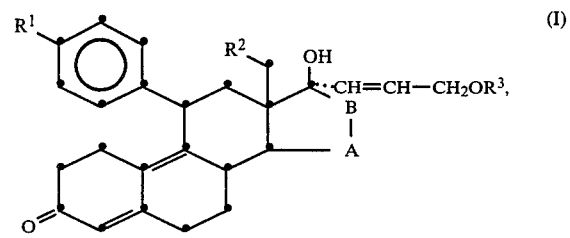

wherein
R$^2$ is a hydrogen atom, a methyl group, or an ethyl group,
R$^3$ is a hydrogen atom or an acyl group,
R$^1$ and A-B have various meanings, which possess antigestagen and antimineralocorticoid activity.

40 Claims, 2 Drawing Figures

11β-ARYLESTRADIENES, THEIR PRODUCTION, AND PHARMACEUTICAL PREPARATIONS CONTAINING SAME

BACKGROUND OF THE INVENTION

This invention relates to novel 11β-arylestradienes, a process for the preparation thereof, to pharmaceutical preparations comprising them and to their use as antigestagens and antimineralocorticoids.

11β-Aryl steroids are known. Thus, for example, 11β-aryl-17α-propynyl- and -ethynyl-4,9(10)-estradienes have been disclosed in European Patent Application No. 82400025.1 (publication number 0057115) and in U.S. Pat. No. 4,386,085 as compounds having antigestagen and antiglucocorticoid properties.

Commonly assigned applications Ser. Nos. 581,853, filed Feb. 21, 1984, and 621,308, filed June 15, 1984, are directed to analogous compounds of the gonane series.

SUMMARY OF THE INVENTION

In a first composition of matter aspect, this invention relates to 11β-arylestradienes of general Formula I wherein
$R^1$ is a hydrogen atom, with $R^I$ and $R^{II}$ meaning hydrogen, alkyl of 1-4 carbon atoms, or acyl of 1-8 carbon atoms, or $R^I$ and $R^{II}$ with inclusion of N meaning a 5- or 6-membered ring wherein, besides N, still another hetero atom, such as O, N, S can be contained in the ring, as well as the corresponding N-oxides and acid addition salts, or $R^I$ and $R^{II}$ with inclusion of N meaning a pyrrole ring optionally substituted by methyl,

—$OR^{III}$ with $R^{III}$ meaning hydrogen, methyl, ethyl, propyl, methoxyphenyl, allyl, or dimethylaminoethyl,

—$SR^{IV}$ with $R^{IV}$ meaning hydrogen, methyl, ethyl, propyl, or dimethylaminoethyl, and —$SiR_3^V$ with $R^V$ meaning methyl, ethyl, propyl, butyl, or benzyl, $R^2$ is a hydrogen atom, a methyl group, or an ethyl group,

$R^3$ is a hydrogen atom or an acyl group of 1-8 carbon atoms, and wherein $R^4$ and $R^6$ each mean alkyl of 1-4 carbon atoms in the α- or β-position, and $R^5$ and $R^7$ each mean an alkylidene group in the E- or Z-configuration, and the $C_{20}/C_{21}$-double bond has a Z- or E-configuration.

In a process aspect, this invention relates to a process for the production of compounds of general Formula I wherein $R^1$, $R^2$, $R^3$ and have the meanings given above and the $C_{20}/C_{21}$-double bond has a Z- or E-configuration, characterized in that, in a compound of general Formula II wherein
$R^1$, $R^2$ and have the meanings given in Formula I, Z is an ethylene group or a 2,2-dimethyltrimethylene group and R is a hydrogen atom or an organic group that can be readily split off in an acidic medium or by hydrogenolysis, the acetylenic triple bond is hydrogenated to the Z-configured $C_{20}/C_{21}$-double bond (III) in the presence of a deactivated noble metal catalyst; or the acetylenic triple bond is conventionally reduced to the E-configured $C_{20}/C_{21}$-double bond (III), and subsequently by treatment with a dilute acid, a pyridinium salt of a strong acid, or an acidic ion exchanger, the 3-ketal blockage is split up, any blocking group R present that can be split off with an acid is removed, and water is split off with formation of the 4,9(10)-dien-3-one system, and optionally thereafter a free 22-hydroxy group is acylated.

In a further composition of matter aspect, this invention relates to pharmaceutical compositions comprising 11$\beta$-arylestradienes of Formula I.

In a method of use aspect, this invention relates to a method of using the 11$\beta$-arylestradienes of Formula I as antigestagens and as antimineralocorticoids.

Upon further study of the specification and appended claims, further objects and advantages of this invention will become apparent to those skilled in the art.

DETAILED DISCUSSION

It has been discovered that the novel compounds of general Formula I possess antigestagen and antimineralocorticoid effects. The simultaneous occurrence of antigestagen and antimineralocorticoid activities in one compound has not been disclosed heretofore. Suprisingly, the two effects occur in the novel compounds even upon oral administration in an effectiveness comparable to the compounds of the prior art. However, it should be noted that in some compounds of this invention, the antigestagen activity and, in others, the antimineralocorticoid activity predominates. In all cases, however, both activities are displayed. The novel compounds of general Formula I are suitable for fertility control as well as for the treatment of pathological conditions which are accompanied by hyperaldosteronism. The antiglucocorticoid effect, found in prior-art compounds, is not found in the compounds of this invention.

For characterization of the antigestagen activity of the compounds of this invention, their abortive activity was determined in tests conducted on groups of female rats (4 per group) each rat weighing about 200 g. After mating had taken place, the start of pregnancy was confirmed by detection of spermatozoa in vaginal smears. The day of confirmation of spermatozoa is considered day 1 of gravidity (=d 1 p.c.).

The animals were treated with a test compound and/or the solvent after nidation of the blastocysts from d 5 p.c. to d 7 p.c. The test compounds were dissolved in a benzyl benzoate-castor oil mixture (proportion 1:9). The vehicle volume per individual dose was 0.2 ml., administered subcutaneously (s.c.). On d 9 p.c., the animals were sacrificed and the uteri examined for implants and absorption sites, photographs were made of all uteri. The absence of an implant was evaluated as abortion.

The superiority of the compounds of this invention was demonstrated by comparison of the biological properties of 11$\beta$-(4-dimethylaminophenyl)-17$\beta$-hydroxy-17$\alpha$-(3-hydroxyprop-1(Z)-enyl)-4,9(10)-estradien-3-one (A); 11$\beta$-(4-dimethylaminophenyl)-17$\beta$-hydroxy-17$\alpha$-(propyn-1-yl)-4,9(10)-estradien-3-one (B) described in European Patent Application No. 82 400 025.1; 11$\beta$-(4-dimethylaminophenyl)-17$\beta$-hydroxy-17$\alpha$-(3-hydroxyprop-1(Z)-enyl)-16$\beta$-methyl-4,9(10)-estradien-3-one (C); 17$\beta$-hydroxy-17$\alpha$-(3-hydroxyprop-1(Z)-enyl)-11$\beta$-(4-methylaminophenyl)-4,9(10)-estradien-3-one (D); and 11$\beta$-(4-dimethylaminophenyl)-17$a\beta$-hydroxy-17$a\alpha$-(3-hydroxyprop-1(Z)-enyl)-D-homo-4,9,16-estratrien-3-one (E):

TABLE 1

| Abortion Test in Gravid Rats | | |
|---|---|---|
| Compound | Dosage mg/Animal/Day s.c. | n Abortion Positive/ n Total |
| A | 10.0 | 4/4 |
|   | 3.0 | 4/4 |
|   | 1.0 | 4/4 |
| B | 10.0 | 4/4 |
|   | 1.0 | 2/4 |
| C | 3.0 | 4/4 |
|   | 1.0 | 4/4 |
| D | 3.0 | 4/4 |
|   | 1.0 | 4/4 |
| E | 3.0 | 4/4 |
|   | 1.0 | 4/4 |

It can be seen from Table 1 that, with a dose of 1.0 mg, only the compounds of this invention, A, C, D, and E, are fully effective in causing abortion.

Figure 1:
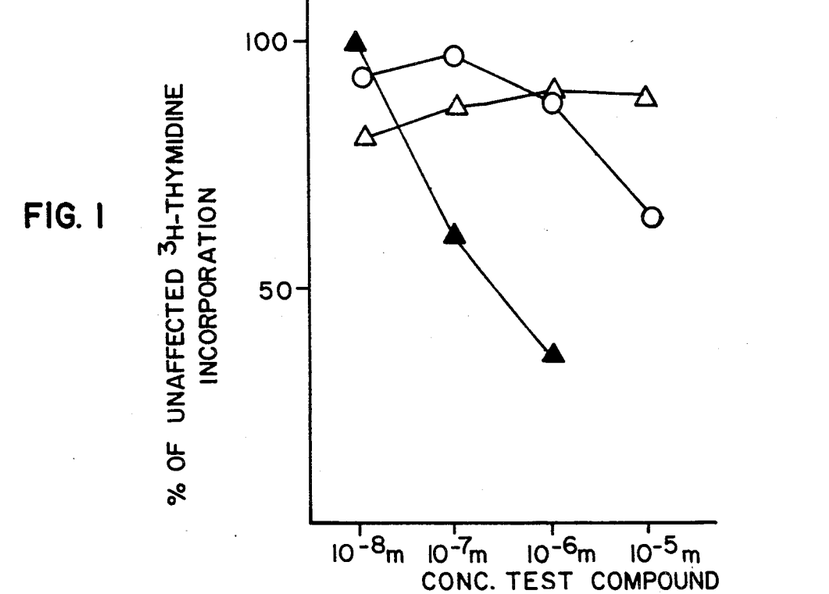
FIG. 1 shows the instrinsic activity of compounds tested on S 49.1 cells.

In order to characterize the glucocorticoid and/or antiglucocorticoid activity, the effect of the compounds of this invention on the DNA synthesis in mouse lymphoma cells was determined. The principle is based on the glucocorticoid sensitivity displayed by T-lymphocytes; this sensitivity is preserved therefrom and can be readily determined quantitatively by incorporation of $^3$H-thymidine. After addition of cortisol to the cultures, the cells showed a dose-dependent inhibition of DNA synthesis (see FIG. 1), a 50% inhibitory effect being achieved with about $10^{-6}$ M cortisol. The intrinsic activity observed for cortisol is plotted as ▲, for compound A as °, and for compound B as ∆.

Figure 2:
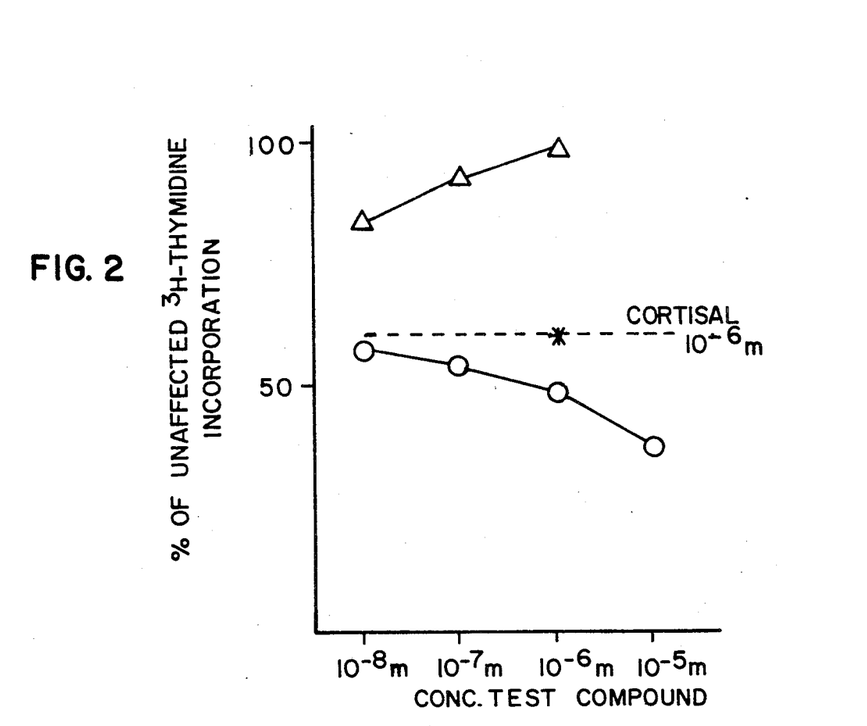
FIG. 2 shows the results obtained when those compounds are tested for antiglucocorticoid activity.

To permit potential agonistic and antagonistic effects of the test compounds to become apparent, the cells were treated simultaneously with $10^{-6}$ M cortisol shown as a dotted line in FIG. 2, and suitable amounts of the test compound (cortisol and the test compounds were dissolved in ethanol, the final concentration in ethanol in the batch was 1%, only ethanol was added to the control samples). The known antiglucocorticoid B shows a dose-dependent elimination of the cortisol-inhibiting effect—an equimolar concentration is capable of neutralizing the effect of $10^{-6}$ M cortisol (see FIG. 2). The compound A of this invention, in contrast thereto, shows no measurable antiglucocorticoid activity (see FIG. 2). Compound B, added by itself to the cultures, shows no agonistic (corticoid-simulating) effect (see FIG. 1). Compound A shows a slight individual activity which, however, amounts to only 1% of the cortisol activity (see FIG. 2).

The antialdosterone test is utilized for evaluating antimineralocorticoid activity of the compounds of this invention. In this test, adrenalectomized, fasting Wistar rats, substituted with fluocortolone and fluocortolone caproate, were treated with 1.0–2.0–4.0 mg of test compound per animal. The test compound was administered orally as a crystalline suspension in NaCl/Myrj 53. One hour after administration, the animals received an intravenous long-term infusion of physiological sodium chloride solution with an addition of 0.15 μg of aldosterone per animal per hour. The excretion of sodium and potassium salts was measured hourly from the third to the tenth hour, and the Na/K quotient as well as the quotient log Na (100)/K were determined.

It was found that the antimineralocorticoid effect of the compounds of this invention is on the same order of magnitude as that of spironolactone.

As compared with the prior-art compounds, the compounds of this invention possess stronger antigestagen activity and an antimineralocorticoid activity, rather than an antiglucocorticoid activity.

The compounds of this invention, as antigestagens, are suitable for eliminating a pregnancy and/or for triggering menstruation. The antimineralcorticoid effect of the compounds does not interfere, and is even desirable in case when hyperaldosteronism is present.

The compounds of the present invention are also useful in the treatment of certain forms of aldosteronism, of hypertonia, of edemas and other disturbances caused by aldosterone.

The present invention also relates to pharmaceutical preparations which contain a compound of Formula I. The pharmacologically effective compounds of this invention can be processed by conventional methods of galenic pharmacy into pharmaceutical preparations for oral or parenteral administration, e.g., to mammals including humans. Conventional excipients are pharmaceutically acceptable organic or inorganic carrier substances suitable for parental, enteral or topical application which do not deleteriously react with the active compounds. Suitable pharmaceutically acceptable carriers include but are not limited to water, salt solutions, alcohols, gum arabic, vegetable oils, polyethylene glycols, geleatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including supporitories. Ampoules are conveninent unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10–100 mg in a pharmaceutically acceptable carrier per unit dosage. The dosage of the compounds according to this invention generally is 10–1,000 mg/day when administered to patients, e.g., humans, preferably 50–500 mg/day to achieve an antimineralocortocoid effect analogous to spironolactone and 20–200 mg/day to induce abortions or trigger menstruation analogous to the known agent RU 486. Suitable dosages and regimens for a given host can be determined using conventional considerations, e.g., by customary comparison of the differential activities of the subject compound and of a known agent, e.g., by means of an appropriate, conventional pharmacological protocol.

The novel 17β-arylestradienes contain, in the 17α-position of the steroid skeleton, a 3-hydroxy- or acyloxy-prop-1-enyl side chain with a Z- or E-configured double bond, respectively. Acyl is understood to mean carboxylic acid residues of 1–8 carbon atoms. Alkanoyl groups are preferred, such as the acetyl, propionyl, butyryl, pentanoyl, hexanoyl, and heptanoyl groups.

In the compounds of general Formula I, the aryl residue in the 11β-position of the steroid skeleton represents a phenyl residue substituted in the para-position by $R_1$. If $R^1$ stands for then $R^I$ and $R^{II}$ are hydrogen or alkyl groups of 1–4 carbon atoms, wherein the methyl group and the ethyl group are preferred. The group also stands for a heterocyclic five- or six-membered ring which can contain, besides N- and C-atoms, also additionally an O- or S-atom; examples are the pyrrolidino, piperidino, piperazino, morpholino, oxa- and thiazolidino, as well as thiadiazolidino rings. Preferably, the rings are fully saturated.

is also understood to include the corresponding N-oxides, such as, for example, dimethylamino-N-oxide, pyrrolidino-, piperidino-, piperazino-, etc. N-oxide, and acid addition salts. Also, is to mean a pyrrole ring optionally substituted by 1–4 methyl groups, e.g. 2,5-dimethyl-pyrrole. When $R^I$ and/or $R^{II}$ is acyl, $C_{1-8}$-alkanoyl groups are preferred.

The dimethylamino and formylamino residues are the preferred groups for $R^1$.

Suitable $R^3$ acyl groups are also $C_{1-8}$-alkanoyl.

The substituent represented in Formula I by $R^4$ and $R^6$ is an alkyl residue of 1–4 carbon atoms, preferably the methyl or ethyl residue; $R^5$ and $R^7$ represent a $C_{1-4}$-alkylidene residue, preferably the ethylidene residue.

Throughout the foregoing, other contemplated alkyl portions include straight chain or branched propyl, butyl, pentyl, hexyl, heptyl or octyl groups.

The novel compounds of general Formula I are prepared according to this invention by the process as set forth above.

In a first step, the triple bond (II) of the 17α-(3-oxygenated 1-propynyl) compound is hydrogenated or reduced to the Z- or E-configured double bond (III), respectively. The compounds of Formula III are novel intermediates and correspond in scope to the compounds of Formula I.

The compound with the Z-configured double bond is produced by hydrogenating the acetylenic triple bond with a deactivated noble metal catalyst (J. Fried, J. A. Edwards: Organic Reactions in Steroid Chemistry, Van Nostrand Reinhold Company 1972, p. 134; and H. O. House: Modern Synthetic Reactions 1972, p. 19). Examples for deactivated noble metal catalysts are 10% palladium on barium sulfate in the presence of an amine (e.g., tertiary), or 5% palladium on calcium carbonate with the addition of lead (II) acetate. The hydrogenation is terminated after absorption of one equivalent of hydrogen.

The compound with the E-configured double bond is formed conventionally by reduction of the acetylenic triple bond. Quite a number of methods for converting alkynes into trans-olefins have been described in the literature, for example reduction with sodium in liquid ammonia (J. Am. Chem. Soc. 63: 216 [1941]); with sodium amide in liquid ammonia (J. Chem. Soc. 1955, 3558); with lithium in low-molecular amines (J. Am. Chem. Soc. 77: 3378 [1955]); with boranes (J. Am. Chem. Soc. 93: 3395 [1971] and 94: 6560 [1971]); with diisobutyl aluminum hydride and methyllithium (J. Am. Chem. Soc. 89: 5085 [1967]); and especially with lithium aluminum hydride/alcoholate (J. Am. Chem. Soc. 89: 4245 [1967]).

Another possibility is the reduction of the triple bond with chromium(II) sulfate in the presence of water or dimethylformamide in a weakly acidic medium (J. Am. Chem. Sox. 86: 4358 [1964]), as well as generally reduction by treatment with transition metal compounds with a change in the oxidation stage.

In order to split off water with the formation of the 4,9(10)-dien-3-one system, and for the simultaneous ketal cleavage and removal of a hydroxy blocking group R that may be present in the 22-position, the 17α-oxypropenyl-17β-hydroxy compound of general Formula III is subsequently treated with an acid, a pyridinium salt, or an acidic ion exchanger.

The hydroxy blocking group, characterized by R in general Formula II or III, is a group that can be readily split off in an acidic medium or by hydrogenolysis, such as, for example, methoxymethyl, ethoxymethyl, tetrahydropyranyl, or benzyl.

The acidic treatment takes place in a manner known per se by dissolving the compound of Formula III, which contains a 3-ketal group and a 5α-hydroxy group and a 17β-(3-hydroxypropenyl) group that is optionally O-blocked, in a with water miscible solvent, such as aqueous methanol, ethanol, or acetone, and treating the solution with catalytic amounts of a mineral or sulfonic acid, such as hydrochloric acid, sulfuric acid, phosphoric acid, perchloric acid, or p-toluenesulfonic acid, or an organic acid, such as acetic acid, until water has been split off and blocking groups have been removed. The reaction, which takes place at temperatures of 0°–100° C., can be performed with an especially high yield by using a pyridinium salt, such as pyridinium tosylate, or an acidic ion exchanger. The course of the reaction is controlled by analytical methods, for example by subjecting withdrawn samples to thin-layer chromatography.

Acylation of the 22-hydroxy group takes place conventionally, for example by reaction with the acid anhydride in pyridine at room temperature.

Suitable acid addition salts of the basic compound of Formula I are prepared conventionally, e.g., by the usual neutralization reactions. Suitable acids include the usual organic and inorganic acids which produce pharmacologically acceptable salts, e.g., HCl, HBr, HI, acetic acid, propionic acid, etc.

The preparation of the starting compounds of general Formula II will be explained with the aid of the reaction scheme set out below:

Oxiranes (1) according to European Patent Application No. 82 400 025.1 (Publication No. 0057115) are reacted with metallized derivatives of propargyl alcohol, for example with 1-lithium-3-tetrahydropyran-2'-yloxy-1-propyne, to the 17α-[3-oxygenated 1-propynyl]-17β-hydroxy compounds (2). Introduction of the 11β-aryl residue takes place, to obtain (II), either by Cu(I)-catalyzed Grignard reaction with the corresponding arylmagnesium halides (Tetrahedron Letters 1979, 2051) or by reaction with mixed organocuprates of the type R₂Cu(CN)Li₂ (J. Am. Chem. Soc. 103: 7672 [1981]). Finally, the ketone (3) can be reacted to (II) according to EP 57115 with free propargyl alcohol in the presence of bases, such as potassium ethylate, potassium tert-butylate, or butyllithium (BuLi).

The preparation of several starting compounds of general Formula II will be described in greater detail below:

1(a) Under ice water cooling, 208 ml of a 15% solution of n-butyllithium in hexane is added dropwise to a solution of 35.7 g of 3-tetrahydropyran-2'-yloxy-1-propyne in 760 ml of absolute tetrahydrofuran. Thereafter, the mixture is stirred for another 15 minutes at +5° to +10° C. and then a solution of 23.7 g of 3,3-(2,2-dimethylpropane-1,3-dioxy)-5α,10α-oxido-9(11)-estren-17-one in 470 ml of absolute THF is added dropwise thereto. The mixture is then stirred for 20 minutes at 25° C., the reaction solution thereupon is poured into about 5 l of ice water and extracted with ethyl acetate. The ethyl acetate extract is dried over sodium sulfate/activated carbon and concentrated under vacuum. After filtration over aluminum oxide with hexane/ethyl acetate as the eluents, 29.3 g of 3,3-(2,2-dimethylpropane-1,3-dioxy)-5α,10α-oxido-17α-[3-(tetrahydropyran-2-yloxy)-1-propynyl]-9(11)-estren-17β-ol is obtained as a colorless oil.

(b) A suspension of 5.28 g of magnesium (filings) in 275 ml of absolute THF is combined in succession with 0.05 ml of methyl iodide and a solution of 50.27 g of 4-bromodimethylaniline in 245 ml of absolute THF. The mixture is agitated in an argon atmosphere until the magnesium is completely dissolved; in this step, the internal temperature is not to rise above 50° C. Subsequently, the mixture is cooled to +5° C., the Grignard solution is combined with 1.12 g of CuCl and stirred for 15 minutes at +5° C. to +10° C. Thereafter a solution of 29.3 g of the product obtained in (a) in 275 ml of absolute THF is added dropwise thereto and the mixture is stirred for 5 hours at room temperature. Then the reaction solution is poured into about 4 l of ice water and extracted with ethyl acetate. Chromatography of the resultant crude product over aluminum oxide with hexane/ethyl acetate yields 32.6 g of 11β-(4-dimethylaminophenyl)-3,3-(2,2-dimethylpropane-1,3-dioxy)-17α-[3-(tetrahydropyran-2-yloxy)-1-propynyl]-9(10)-estrene-5α,17β-diol as a yellowish oil.

2(a) According to 1(a), 22.6 g of 3,3-(2,2-dimethylpropane-1,3-dioxy)-18-methyl-5α,10α-oxido-9(11)-estren-17-one (mp 156°-158° C.) is reacted with 1-lithio-3-(tetrahydropyran-2-yloxy)-1-propyne, thus obtaining 25.4 g of 3,3-(2,2-dimethylpropane-1,3-dioxy)-18-methyl-5α,10α-oxido-17α-[3-(tetrahydropyran-2-yloxy)-1-propynyl]-9(11)-estren-17β-ol as a colorless oil.

(b) At 25° C., 0.1 ml of methyl iodide is first added dropwise to a suspension of 4.3 g of magnesium (filings) in 40 ml of absolute THF, then a solution of 40 g of p-dimethyl-aminoethoxyphenyl bromide (prepared according to D. Lednicer et al., J. Med. Chem. 8: 52 [1964]) in 200 ml of absolute THF is added dropwise thereto. The mixture is stirred until the magnesium is completely dissolved at a bath temperature of maximally 70° C. After cooling to 0° C., 820 mg of CuCl is added, and the mixture is stirred for 20 minutes at 0° C. Then a solution of 15.9 g of the product obtained in (a) in 120 ml of absolute THF is added dropwise thereto. The mixture is stirred for 16 hours at 25° C., poured into ice water, and extracted with ethyl acetate. Chromatography over aluminum oxide (neutral, III) with hexane/ethyl acetate yields 17.1 g of 11β-(4-dimethylaminophenyl)-3,3-(2,2-dimethylpropane-1,3-dioxy)-18-methyl-17α-[3-(tetrahydropyran-2-yloxy)-1-propynyl]-9(10) estrene-5α,17β-diol as a yellowish oil.

3. A Grignard reagent is prepared from 2.4 g of magnesium in 120 ml of absolute THF and 11.6 ml of 4-bromoanisole, as described in 1(b), and combined with 260 mg of CuCl. A solution of 6.4 g of the adduct prepared in 1(a) in 80 ml of absolute THF is added dropwise at 0° C. The reaction solution is stirred for 4 hours at 25° C. and worked up as set forth in 1(b), thus obtaining 7.15 g of 3,3-(2,2-dimethylpropane-1,3-dioxy)-11β-(4-methoxyphenyl)-17α-[3-(tetrahydropyran-2-yloxy)-1-propynyl]-9(10)-estrene-5α,17β-diol as an oily product.

4(a) Under the conditions of 1(a), the organolithium compound is prepared from 6.7 g of propargyl tetrahydropyranyl ether in 100 ml of THF and 40 ml of n-butyllithium (15% in hexane), and reacted with 4.63 g of 3,3-(2,2-dimethylpropane-1,3-dioxy)-16β-methyl-5α,10α-oxido-9(11)-estren-17-one. Chromatography yields 4.22 g of 3,3-(2,2-dimethylpropane-1,3-dioxy)-16β-methyl-5α,10α-oxido-17α-[3-(tetrahydropyran-2-yloxy)prop-1-ynyl]-9(11)-estren-17β-ol as a crystalline mixture of isomers, mp 156°-166° C.

(b) Under the conditions of 1(b), a Grignard reagent is prepared from 1.23 g of magnesium filings in 100 ml of absolute THF, 11.48 g of 4-dimethylaminophenyl bromide in 50 ml of absolute THF, 0.03 ml of methyl iodide, and 230 mg of CuCl, and reacted with 3.55 g of 3,3-(2,2-dimethylpropane-1,3-dioxy)-16β-methyl-5α,10α-oxido-17α-(3-tetrahydropyran-2-yloxy)prop-1-ynyl]-9(11)-estren-17β-ol. Chromatography yields 3.56 g of 11β-(4-dimethylaminophenyl)-3,3-(2,2-dimethylpropane-1,3-dioxy)-16β-methyl-17α-[3-(tetrahydropyran-2-yloxy)prop-1-ynyl]-9(10)-estrene-5α,17β-diol as an oily mixture of isomers.

5. A solution of 10.5 g of 4-(2,5-dimethylpyrrol-1-yl)-bromobenzene (prepared according to J. Chem. Soc. 1951: 3155) in 40 ml of absolute tetrahydrofuran is added dropwise to a suspension of 1.02 g of magnesium filings and 0.05 ml of methyl iodide in 25 ml of absolute tetrahydrofuran in such a way that the temperature, after onset of reaction, does not exceed 45° C. After dissolution of the magnesium, the mixture is cooled to 0° C., 210 mg of CuCl is added, the mixture is stirred for 15 minutes at 0° C., and finally a solution of 4.00 g of 3,3-(2,2-dimethylpropane-1,3-dioxy)-5α,10α-oxido-17α-[3-(tetrahydropyran-2-yloxy)prop-1-ynyl]-9(11)-estren-17β-ol in 50 ml of absolute tetrahydrofuran is added dropwise. After agitation overnight at room temperature, the reaction mixture is poured on ice water and extracted with ethyl acetate. Chromatography on Al$_2$O$_3$ (neutral, III) with hexane/ethyl acetate yields 4.42 g of 3,3-(2,2-dimethylpropane-1,3-dioxy)-11β-[4-(2,5-dimethylpyrrol-1-yl)phenyl]-17α-[3-(tetrahydropyran-2-yloxy)prop-1-ynyl]-9(10)-estrene-5α,17β-diol as a pale-yellow, solid foam.

6. 1.46 g of magnesium filings and 0.05 ml of methyl iodide are combined with 15 ml of absolute tetrahydrofuran. Then a solution of 14.5 g of N-(4-bromophenyl)-piperidine (prepared according to J. Am. Chem. Soc. 75: 5280 [1953]) in 100 ml of absolute tetrahydrofuran is added dropwise in such a way that the temperature, after onset of reaction, does not rise above 45° C. After the magnesium is dissolved, the mixture is cooled to 0° C., 450 mg of CuCl is added thereto, the mixture is stirred at 0° C. for 15 minutes, and finally a solution of 6.0 g of 3,3-(2,2-dimethylpropane-1,3-dioxy)-5α,10α-oxido-17α-[3-(tetrahydropyran-2-yloxy)prop-1-ynyl]-9(11)-estren-17β-ol in 50 ml of absolute tetrahydrofuran is added dropwise thereto. The mixture is then agitated overnight at room temperature, the reaction mixture is poured on ice water and extracted with ethyl acetate. Chromatography on Al$_2$O$_3$ (neutral, III) with hexane/ethyl acetate yields 7.0 g of 3,3-(2,2-dimethylpropane-1,3-dioxy)-11β-(4-piperidinophenyl)-17α-[3-(tetrahydropyran-2-yloxy)prop-1-ynyl]-9(10)-estrene-5α,17β-diol as a colorless, solid foam.

7. 2.16 g of magnesium filings and 0.05 ml of methyl iodide are combined with 15 ml of absolute tetrahydrofuran. Then a solution of 13.5 g of N-(4-bromophenyl)-pyrrolidine (prepared according to J. Am. Chem. Soc. 75: 5280 [1953]) in 150 ml of absolute tetrahydrofuran is added dropwise thereto in such a way that the temperature of the reaction mixture, after onset of reaction, does not exceed 45° C. After the magnesium is dissolved, the mixture is cooled to 0° C., 450 mg of CuCl is added, and the mixture is stirred for 15 minutes at 0° C. and finally a solution of 6.0 g of 3,3-(2,2-dimethylpropane-1,3-dioxy)-5α,10α-oxido-17α-[3-(tetrahydropyran-2-yloxy)-prop-1-ynyl]-9(11)-estren-17β-ol in 70 ml of absolute tetrahydrofuran is added dropwise thereto. Subsequently the mixture is agitated overnight at room temperature, the reaction mixture is poured on ice water, and extracted with ethyl acetate. Chromatography on Al$_2$O$_3$ (neutral, III) with hexane/ethyl acetate thus yields 7.0 g of 3,3-(2,2-dimethylpropane-1,3-dioxy)-11β-[4-(pyrrolidin-1-yl)phenyl]-17α-[3-(tetrahydropyran-2-yloxy)prop-1-ynyl]-9(10)-estrene-5α,17β-diol as a colorless, solid foam.

8. A solution of 2.4 g of 11β-(4-dimethylaminophenyl)-3,3-ethylenedioxy-5α-hydroxy-9-estren-17-one (European Patent Application, publication number 57 115 [82]) in 36 ml of anhydrous tetrahydrofuran is combined at 0° C. with 9.35 g of potassium ethylate. Within 20 minutes, a solution of 3.6 ml of propargyl alcohol in 3.6 ml of tetrahydrfuran is added dropwise and the mixture is further stirred at room temperature for 2 hours under argon. The reaction solution is cooled to 0° C. and combined with about 8 ml of ice-cold 30% sulfuric acid until a weakly acidic reaction is obtained. In this process, the internal temperature of the flask must not rise beyond 20° C. Finally, the solution is neutralized with sodium bicarbonate solution and poured on water. The mixture is extracted three times with ethyl acetate, the extracts are washed neutral, dried over sodium sulfate, and concentrated to dryness under vacuum. The crude product is chromatographed on 300 g of silica gel with a methylene chloride-acetone gradient (0–25% acetone).

Yield: 1.4 g of 11β-(4-dimethylaminophenyl)-3,3-ethylenedioxy-17α-(3-hydroxy-1-propynyl)-9-estrene-5α,17β-diol, mp 130°–132° C.

$[\alpha]_D^{25} = -44°$.

EXAMPLE 1

11β-(4-Dimethylaminophenyl)-17β-hydroxy-17α-(3-hydroxyprop-1(Z)-enyl)-4,9(10)-estradien-3-one (a) A solution of 2.23 g (3.5 mmol) of 3,3-(2,2-dimethylpropane-1,3-dioxy)-11β-(4-dimethylaminophenyl)-17α-[3-(tetrahydropyran-2-yloxy)prop-1-ynyl]-9(10)-estrene-5α,17β-diol in 100 ml of ethanol and 2 ml of triethylamine is hydrogenated, with the addition of 200 mg of Pd/BaSO$_4$ (10%) at room temperature and under normal pressure. After absorption of 80 ml of hydrogen, the reaction is terminated, the product filtered off from the catalyst, concentrated, and the residue chromatographed on Al$_2$O$_3$ (III, neutral) with n-hexane/ethyl acetate, thus obtaining 1.50 g of 3,3-(2,2-dimethylpropane-1,3-dioxy)-11β-(4-dimethylaminophenyl)-17α-[3-(tetrahydropyran-2-yloxy)prop-1(Z)-enyl]-9(10)-estrene-5α,17β-diol as a colorless foam.

$^1$H NMR (CDCl$_3$): δ=5.3–5.8 ppm (m,

---

$^1$H NMR (CDCl$_3$): δ = 5.3–5.8 ppm (m, —C=C—, $J_{cis}$ = 12 Hz) 90 MHz

---

$J_{cis}$=12 Hz) 90 MHz.

(b) 1.1 g (1.7 mmol) of the product obtained in (a) is agitated overnight at room temperature in 10 ml of 70% acetic acid under argon. Subsequently the mixture is stirred for one hour at 50° C. to complete the reaction. For working-up purposes, the product is poured on a mixture of 25 g of ice/10 ml of concentrated aqueous ammonia and extracted with ethyl acetate. After drying over Na$_2$SO$_4$, the product is concentrated and chromatographed on silica gel with n-hexane/ethyl acetate, thus obtaining 0.42 g of 11β-(4-dimethylaminophenyl)-17β-hydroxy-17α-(3-hydroxyprop-1(Z)-enyl)-4,9(10)-estradien-3-one as a lemon-yellow, solid foam. $[\alpha]_D$ (CHCl$_3$)=+203.5°.

EXAMPLE 2

11β-(4-Dimethylaminophenyl)-17β-hydroxy-17α-(3-hydroxyprop-1(E)-enyl)-4,9(10)-estradien-3-one (a) Under argon, 4.8 g (60.13 mol) of lithium aluminum hydride is added in portions to a solution of 4.0 g (6.3 mmol) of 3,3-(2,2-dimethylpropane-1,3-dioxy)-11β-(4-dimethylaminophenyl)-17α-[3-(tetrahydropyran-2-yloxy)prop-1-ynyl]-9(10)-estrene-5α,17β-diol in 100 ml of absolute tetrahydrofuran. Thereafter the reaction mixture is stirred for 2 hours at room temperature and subsequently for one hour at 50° C. Under ice cooling, 4.8 ml of water, 4.8 ml of 4N NaOH, and 14.4 ml of water are then added dropwise in succession. The thus-formed sediment is made into a slurry with a water-/ethyl acetate mixture, vacuum-filtered through a porous plate, and thoroughly washed with ethyl acetate. The ethyl acetate phase is dried with Na₂SO₄, concentrated, and chromatographed with n-hexane/ethyl acetate on Al₂O₃ (III, neutral), thus obtaining 1.05 g of 3,3-(2,2-dimethylpropane-1,3-dioxy)-11β-(4-dimethylaminophenyl)-17α-(3-hydroxyprop-1(E)-enyl)-9(10)-estrene-5α,17β-diol as a colorless foam.

¹H NMR (CDCl₃): δ=5.5–6.0 ppm (m,

---

¹H NMR (CDCl₃): δ = 5.5–6.0 ppm $J_{trans}$ = 15 Hz) 90 MHz.

---

(b) 1.0 g (1.8 mmol) of the product obtained in (a) is stirred overnight at room temperature under argon in 30 ml of 70% acetic acid. The solution is poured on a mixture of 25 g of ice/10 ml of concentrated aqueous ammonia and extracted with ethyl acetate. After drying over Na₂SO₄, the mixture is concentrated and chromatographed on silica gel with n-hexane/ethyl acetate, thus obtaining 0.59 g of 11β-(4-dimethylaminophenyl)-17β-hydroxy-17α-(3-hydroxyprop-1(E)-enyl)-4,9(10)-estradien-3-one as a lemon-yellow, solid foam. $[\alpha]_D$ (CHCl₃)= +157.3°.

EXAMPLE 3

17β-Hydroxy-17α-(3-hydroxyprop-1(Z)-enyl)-11β-(4-methylaminophenyl)-4,9(10)-estradien-3-one (a) A solution of 2.6 g of the product prepared in Example 1(a) in 100 ml of methylene chloride is stirred with the addition of 3.55 g of pyrolusite (MnO₂) for 6 hours at room temperature. After vacuum-filtering, the mixture is washed with methylene chloride, concentrated, and chromatographed with n-hexane/ethyl acetate on Al₂O₃ (III, neutral), thus obtaining, besides 1.3 g of starting material, 0.86 g of 3,3-(2,2-dimethylpropane-1,3-dioxy)-11β-(4-methylaminophenyl)-17α-[3-(tetrahydropyran-2yloxy)prop-1(Z)-enyl]-9(10)-estrene-5α17β-diol as a colorless. solid foam.

(b) 0.86 of the product obtained in (a) is stirred under argon in 8.6 ml of 70% acetic acid overnight at room temperature. To complete the reaction, agitation is then continued for 1.5 hours at 50° C. The mixture is subsequently poured on water and brought to pH 10 with concentrated aqueous ammonia. The mixture is extracted with methylene chloride, washed neutral with water, dried over Na₂SO₄, concentrated, and the residue chromatographed with n-hexane/ethyl acetate on Al₂O₃ (III, neutral). Yield: 0.25 g of 17β-hydroxy-17α-(3-hydroxyprop-1(Z)-enyl)-11β-(4-methylaminophenyl)-4,9(10)-estradien-3-one as a lemon-yellow, solid foam.

¹H NMR (CDCl₃): δ=6.98; 6.52 (dd, 4H, aromatic C—H, J=8 Hz), 5.7–5.6 (m, 2H, —CH=CH—, $J^{cis}$=12.5 Hz), 5.74 (s, 1H, H-4), 4.4–4.2 (m, 2H, —CH₂OH) 2.80 (s, 3H, —NCH₃) 0.62 (s, 3H, CH₃).

Alternative Preparation:

Preparation of p-Bromo-N-methyl-N-trimethylsilylaniline

Under a protective gas, a lithium diisopropylamide solution produced from 12.12 g of diisopropylamine in 100 ml of absolute tetrahydrofuran and 68 ml of 1.6-molar n-butyllithium/n-hexane is added dropwise at a temperature of −50° C. to 20 g of p-bromo-N-methylaniline in 50 ml of absolute tetrahydrofuran, thus forming a colorless precipitate. After continuing agitation for 1 hour at −20° C., 11.6 g (=13.5 ml) of trimethylsilyl chloride is added dropwise to the reaction mixture, thus again dissolving the precipitate. The mixture is stirred for 16 hours at room temperature. The lithium chloride forming during the reaction is suctioned off, the filtrate is concentrated, and the residue is distilled with a water-jet aspirator, thus obtaining 23.9 g of p.bromo-N-methyl-N-trimethylsilylaniline, bp (16 torr) 131°–135° C.

(a) Under argon, 23.9 g of p-bromo-N-methyl-N-trimethylsilylaniline in 10 ml of absolute tetrahydrofuran is added dropwise to a suspension of 2.25 g of magnesium in 20 ml of absolute tetrahydrofuran and 0.1 ml of methyl iodide. A weakly exothermic reaction is observed and, to dissolve the magnesium entirely, the mixture is stirred for another 4 hours at +50° C., then cooled to +5° C., and 1 g of copper chloride is added. After another 15 minutes of agitation, 10 g of 3,3-(2,2-dimethylpropane-1,3-dioxy)-5α,10α-epoxy-17α-[3-(tetrahydropyran-2-yloxy)prop-1-ynyl]-9(11)-estren-17β-ol in 50 ml of absolute tetrahydrofuran is added dropwise thereto. The mixture is stirred for 20 hours at room temperature and, for working-up purposes, poured into 100 g of ice/10 ml of saturated ammonium chloride solution, and extracted with ethyl acetate. The organic phases are washed neutral with water and dried over sodium sulfate. The concentrated residue is chromatographed on Al₂O₃ (III, neutral) with n-hexane/ethyl acetate, thus obtaining 10.7 g of 3,3-(2,2-dimethylpropane-1,3-dioxy)-11β-(4-methylaminophenyl)-17α-[3-(tetrahydropyran-2-yloxy)prop-1-ynyl]-9(10)estrene-5α,17β-diol as a colorless, solid foam.

(b) Under normal conditions, 10.7 g of the compound obtained in (a) is hydrogenated in 250 ml of absolute ethanol and 9.6 ml of triethylamine in the presence of 0.96 g of palladium/BaSO₄ (10%). The reaction is terminated after absorption of 300 ml of hydrogen, the catalyst is filtered off, the mixture is concentrated, and the residue is chromatographed on Al₂O₃ (III, neutral) with n-hexane/ 10–70% ethyl acetate, thus obtaining 6.3 g of 3,3-(2,2-dimethylpropane-1,3-dioxy)-11β-(4-methylaminophenyl)-17α-[3-(tetrahydropyran-2-yloxy)prop-1(Z)-enyl]-9(10)-estrene-5α,17β-diol as a colorless, solid foam.

---

¹H NMR (CDCl₃): δ = 6.98; 6.52 ppm (dd, 4H, arom. C—H,
90 MHz   J = 8 Hz)
5.7–5.6 (m, 2H, —CH=CH—, -continued $J_{cis} = 12.5$ Hz)

(c) 4.25 g of the product obtained in (b) is dissolved in 100 ml of 70% acetic acid and agitated for one hour at 50° C. Then the mixture is stirred into 100 g of ice/100 ml of concentrated aqueous ammonia solution, and extracted with ethyl acetate. The organic phases are washed neutral with water and dried over sodium sulfate. After concentration, the mixture is chromatographed on silica gel with an n-hexane/ethyl acetate mixture, yielding 1.86 g of 17β-hydroxy-17α-(3-hydroxyprop-1(Z)-enyl)-11β-(4-methylaminophenyl)-4,9(10)-estradien-3-one as a lemon-yellow, solid foam. [α]$_D$ (CHCl$_3$) = +196.2°.

EXAMPLE 4

11β-(4-Aminophenyl)-17β-hydroxy-17α-(3-hydroxyprop-1(Z)-enyl)-4,9(10)-estradien-3-one (a) Under argon, a solution of 18.5 g of N,N-bis[trimethylsilyl]-4-bromoaniline (J. Org. Chem. 40: 1090 [1975]) in 50 ml of absolute tetrahydrofuran is added to a suspension of 2.64 g of magnesium and 0.05 ml of methyl iodide in 20 ml of absolute tetrahydrofuran in such a way that the temperature, after onset of reaction, does not exceed 45° C. After the magnesium is completely dissolved, the mixture is cooled to 0° C., 500 mg of CuCl is added, and the mixture is stirred for 15 minutes at 0° C. Thereafter a solution of 6.0 g of 3,3-(2,2-dimethylpropane-1,3-dioxy)-5α,10α-epoxy-17α-[3-(tetrahydropyran-2-yloxy)prop-1-ynyl]-9(11)-estren-17β-ol in 80 ml of absolute tetrahydrofuran is added dropwise thereto, and the reaction mixture is stirred for 16 hours at room temperature. For working-up purposes, the mixture is poured into aqueous ammonia solution and extracted with ethyl acetate. After drying the organic phase over Na$_2$SO$_4$, it is filtered, concentrated, and the residue is stirred for 4 hours at 50° C. under argon in 200 ml of 20% ethanolic potassium hydroxide solution. Subsequently the mixture is stirred into an ice/water mixture and extracted with ethyl acetate. The organic phase is washed neutral with water and dried over Na$_2$SO$_4$. After concentration, the product is chromatographed on Al$_2$O$_3$ (III, neutral) with hexane/ethyl acetate, thus obtaining 5.27 g of 11β-(4-aminophenyl)-3,3-(2,2-dimethylpropane-1,3-dioxy)-17α-[3-(tetrahydropyran-2-yloxy)prop-1-ynyl]-9(10)-estrene-5α,17β-diol as a colorless, solid foam.

(b) 3.8 g of the product obtained in (a) is hydrogenated in 100 ml of ethanol and 3.6 ml of triethylamine with the addition of 360 mg of palladium/BaSO$_4$ (10%) under normal conditions. After absorption of 141 ml of hydrogen, the reaction is terminated, the mixture filtered off from the catalyst, concentrated, and the residue is chromatographed with n-hexane/ethyl acetate on Al$_2$O$_3$ (III, neutral), thus producing 2.98 g of 11β-(4-aminophenyl)-3,3-(2,2-dimethylpropane-1,3-dioxy)-17α-[3-(tetrahydropyran-2-yloxy)prop-1(Z)-enyl]-9(10)-estrene-5α,17β-diol as a colorless, solid foam.

$^1$H NMR (CDCl$_3$): δ = 5.3–5.7 ppm

90 MHz (c) Under argon, 2.97 g of the product obtained in (b) is stirred overnight at room temperature in 50 ml of 70% acetic acid. To work up the reaction mixture, it is poured on 50 g of ice/50 ml of concentrated ammonia water and extracted with ethyl acetate. After drying over Na$_2$SO$_4$, the mixture is concentrated and the residue is chromatographed on silica gel with n-hexane/ethyl acetate, thus obtaining 1.57 g of 11β-(4-aminophenyl)-17β-hydroxy-17α-(3-hydroxyprop-1(Z)-enyl)-4,9(10)-estradien-3-one as a lemon-yellow, solid foam. [α]$_D$ (CHCl$_3$) = +185.7°.

EXAMPLE 5

11β-(4-Dimethylaminophenyl)-17β-hydroxy-17α-(3-hydroxyprop-1(Z)-enyl)-16β-methyl-4,9(10)-estradien-3-one (a) 2.67 g (4.1 mmol) of 3,3-(2,2-dimethylpropane-1,3-dioxy)-11β-(4-dimethylaminophenyl)-16β-methyl-17α-[3-(tetrahydropyran-2-yloxy)prop-1-ynyl]-9(10)-estrene-5α,17β-diol is hydrogenated at room temperature under normal pressure in 100 ml of ethanol with the addition of 2.3 ml of triethylamine and 235 mg of Pd/BaSO$_4$ (10%). After absorption of 100 ml of hydrogen, the product is filtered off from the catalyst, concentrated, and the residue chromatographed on Al$_2$O$_3$ (III, neutral) with n-hexane/ethyl acetate, thus obtaining 1.9 g of 3,3-(2,2-dimethylpropane-1,3-dioxy)-11β-(4-dimethylaminophenyl)-16β-methyl-17α-[3-(tetrahydropyran-2-yloxy)prop-1(Z)-enyl]-9(10)-estrene-5α,17β-diol as a colorless, solid foam.

$^1$H NMR (CDCl$_3$): δ = 5.3–5.7 ppm (m, —C(H)=C(H)—)

90 MHz

(b) Under argon, 1.9 g (2.9 mmol) of the product obtained in (a) is agitated overnight at room temperature in 40 ml of 70% acetic acid. To work up the reaction mixture, it is poured on 40 g of ice/40 ml of concentrated ammonia water and extracted with ethyl acetate. After drying over Na$_2$SO$_4$, the product is concentrated and the residue chromatographed on silica gel with n-hexane/ethyl acetate, thus obtaining 0.92 g of 11β-(4-dimethylaminophenyl)-17βhydroxy-17α-(3-hydroxyprop-1(Z)-enyl)-16β-methyl-4,9(10)estradien-3-one as a lemon-yellow, solid foam. [α]D (CHCl$_3$) = +210.8°.

EXAMPLE 6

11β-(4-Dimethylaminophenyl)-17β-hydroxy-17α-(3-hydroxyprop-1(Z)-enyl)-16α-methyl-4,9(10)-estradien-3-one (a) 700 mg (1.08 mmol) of 3,3-(2,2-dimethylpropane-1,3-dioxy)-11β-(4-dimethylaminophenyl)-16α-methyl-17α-[3-(tetrahydropyran-2-yloxy)prop-1-ynyl]-9(10)-estrene-5α,17β-diol is hydrogenated in 100 ml of ethanol at room temperature under normal pressure with the addition of 0.62 ml of triethylamine and 62 mg of Pd/BaSO$_4$ (10%). The mixture is filtered off from the catalyst after absorption of 24 ml of hydrogen, concentrated, and the residue chromatographed on Al$_2$O$_3$ (III, neutral) with n-hexane/ethyl acetate, thus obtaining 525 mg of 3,3-(2,2-dimethylpropane-1,3-dioxy)-11β-(4-dimethylaminophenyl)-16α-methyl-17α-[3-(tetrahydropyran-2-yloxy)prop-1(Z)-enyl]-9(10)-estrene-5α,17β-diol as a colorless, solid foam.

$^1$H NMR (CDCl$_3$): δ = 5.4–5.8 ppm (m, —C=C—, J$_{cis}$ = 12.5 Hz) 90 MHz

(b) Under argon, 500 mg (0.77 mmol) of the product obtained in (a) is stirred overnight at room temperature in 20 ml of 70% acetic acid. Working up is performed by pouring on 20 g of ice/20 ml of concentrated aqueous ammonia, and extraction with ethyl acetate. After drying over Na$_2$SO$_4$, the mixture is concentrated and the residue chromatographed on silica gel with n-hexane/ethyl acetate, yielding 289 mg of 11β-(4-dimethylaminophenyl)-17β-hydroxy-17α-(3-hydroxyprop-1(Z)-enyl)-16α-methyl-4,9(10)-estradien-3-one as a lemon-yellow, solid foam. [α]$_D$ (CHCl$_3$) = +194.6°.

EXAMPLE 7

7α-(3-hydroxyprop-1(Z)-enyl)-11β-17β-Hydroxy-1[4-(piperidin-1-yl)phenyl]-4,9(10)-estradien-3-one (a) 5.3 g (7.9 mmol) of 3,3-(2,2-dimethylpropane-1,3-dioxy)-11β-[4-(piperidin-1-yl)phenyl]-17α-[3-(tetrahydropyran-2-yloxl)prop-1-ynyl]-9(10)-estrene-5α,17β-diol is hydrogenated at room temperature under normal pressure in 220 ml of ethanol with the addition of 4.5 ml of triethylamine and 450 mg of Pd/BaSO$_4$ (10%) After absorption of 180 ml of hydrogen, the mixture is filtered off from the catalyst, concentrated, and the residue chromatographed on Al$_2$O$_3$ (III, neutral) with n-hexane/ethyl acetate, thus obtaining 3.41 g of 3,3-(2,2-dimethylpropane-1,3-dioxy)-11β-[4-(piperidin-1-yl)phenyl]-17α-[3-(tetrahydropyran-2-yloxy)prop-1(Z)-enyl]-9(10)-estrene-5α,17β-diol as a colorless, solid foam. $^1$H NMR (CDCl$_3$): δ=5.3–5.8 ppm (m, $^1$H NMR (CDCl$_3$): δ = 5.3–5.8 ppm 90 MHz (m, —C=C—; J$_{cis}$ = 12 Hz)

J$_{cis}$=12 Hz) 90 MHz.

(b) 3.37 g (5 mmol) of the product obtained in (a) is stirred overnight at room temperature under argon in 60 ml of 70% acetic acid. Thereafter the mixture is agitated for one hour at 50° C. Working up of the mixture is performed by pouring on 60 g of ice/60 ml of concentrated aqueous ammonia, and extraction with ethyl acetate. After drying over Na$_2$SO$_4$, the mixture is concentrated, and the residue is chromatographed on silica gel with n-hexane/ethyl acetate, thus producing 1.75 g of 17β-hydroxy-17α-(3-hydroxyprop-1(Z)-enyl)-11β-[4-(piperidin-1-yl)phenyl]-4,9(10)-estradien-3-one as a lemon-yellow, solid foam. [α]$_D$ (CHCl$_3$) = +209 °.

EXAMPLE 8

17β-Hydroxy-17α-(3-hydroxyprop-1(Z)-enyl)-11β-[4-(pyrrolidin-1-yl)phenyl]-4,9(10)-estradien-3-one (a) 4.36 g (6.6 mmol) of 3,3-(2,2-dimethylpropane1,3-dioxy)-11β-[4-(pyrrolidin-1-yl)phenyl]-17α-[3-(tetrahydropyran-2-yloxy)prop-1-ynyl]-9(10)-estrene-5α,17β-diol is hydrogenated in 200 ml of ethanol with the addition of 3.8 ml of triethylamine and 380 mg of Pd/BaSO$_4$ (10%) at room temperature under normal pressure. After absorption of 160 ml of hydrogen, the mixture is filtered off from the catalyst, concentrated, and the residue chromatographed on Al$_2$O$_3$ (III, neutral) with n-hexane/ethyl acetate, thus obtaining 2.91 g of 3,3-(2,2-dimethylpropane-1,3-dioxy)-11β-[4-(pyrrolidin-1-yl)phenyl]-17α-[3-(tetrahydropyran-2-yloxy)prop-1(Z)-enyl]-9(10)-estrene-5α,17β-diol as a colorless, solid foam.

$^1$H NMR (CDCl$_3$): δ=5.3–5.8 ppm (m, $^1$H NMR (CDCl$_3$): δ = 5.3–5.8 ppm (m, —C=C—, J$_{cis}$ = 12 Hz) 90 MHz J$_{cis}$=12 Hz) 90 MHz.

(b) 2.91 g (4.4 mmol) of the product obtained in (a) is stirred in 50 ml of 70% acetic acid for 5 hours at 50° C. In order to work up the reaction mixture, it is poured on 50 g of ice/50 ml of concentrated ammonia water and extracted with ethyl acetate. After drying over Na$_2$SO$_4$, the mixture is concentrated and the residue chromatographed on silica gel with n-hexane/ethyl acetate, thus obtaining 1.66 g of 17β-hydroxy-17α-(3-hydroxyprop-1(Z)-enyl)-11β-[4-(pyrrolidin-1-yl)phenyl]-4,9(10)-estradien-3-one as a lemon-yellow, solid foam.

[α]$_D$ (CHCl$_3$) = +214.1°.

EXAMPLE 9

11β-[4-(2,5-Dimethylpyrrol-1-yl)-phenyl]-17β-hydroxy-17α-(3-hydroxyprop-1(Z)-enyl)-4,9(10)-estradien-3-one (a) 1.4 g (2.1 mmol) of 3,3-(2,2-dimethylpropane1,3-dioxy)-11β-[4-(2,5-dimethylpyrrol-1-yl)phenyl]-17α-[3-(tetrahydropyran-2-yloxy)prop-1-ynyl]-9(10)-estrene-5α,17β-diol is hydrogenated in 60 ml of ethanol with the addition of 1.2 ml of triethylamine and 120 mg of Pd/BaSO$_4$ (10%) at room temperature and under normal pressure. After absorption of 48 ml of hydrogen, the mixture is filtered off from the catalyst, concentrated, and the residue chromatographed on Al$_2$O$_3$ (III, neutral) with n-hexane/ethyl acetate, yielding 758 mg of 3,3-(2,2-dimethylpropane-1,3-dioxy)-11β-[4-(2,5-dimethylpyrrol-1-yl)phenyl]-17α-[3-(tetrahydropyran2-yloxy)-prop-1(Z)-enyl]-9(10)-estrene-5α,17β-diol as a colorless, solid foam.

$^1$H NMR (CDCl$_3$): δ=5.4–5.8 ppm (m, $^1$H NMR (CDCl$_3$): δ = 5.4–5.8 ppm (m, —C=C—)

90 MHz

90 MHz.

(b) Under argon, 2.57 g (3.7 mmol) of the product obtained according to (a) is stirred in 50 ml of ethanol with the addition of 300 mg of p-toluenesulfonic acid monohydrate for 2 hours at room temperature. The reaction mixture is worked up by pouring on 50 ml of ice water/5 ml of concentrated ammonia solution, and extraction with ethyl acetate. After drying over Na$_2$SO$_4$, the mixture is concentrated and the residue chromatographed on silica gel with n-hexane/ethyl acetate, thus obtaining 0.85 g of 11β-[4-(2,5-dimethylpyrrol-1-yl)phenyl]-17β-hydroxy-17α(3-hydroxyprop-1(Z)-enyl)-4,9(10)-estradien-3-one as a yellow, solid foam.

$[\alpha]_D$ (CHCl₃) = +152.4°.

EXAMPLE 10

11β-(4-Dimethylaminophenyl)-16(E)-ethylidene-17β-hydroxy-17α-(3-hydroxyprop-1(Z)-enyl)-4,9(10)-estradien-3-one

- (a) A suspension of 29.3 g of 3,3-(2,2-dimethylpropane-1,3-dioxide-5(10),9(11)-estradien-17-one and 28.6 g of bis-(dimethylamino)-tert-butoxymethane is stirred under argon for 60 minutes at 160° C. After cooling, the crude product is triturated with about 50 ml of ethyl acetate, filtered, and the filter residue recrystallized from ethyl acetate. In this way 27.6 g of 16-dimethylaminomethylene-3,3-(2,2-dimethylpropane-1,3-dioxy)-5(10),9(11)-estradien-17-one is obtained, mp 208°–211° C.

(b) A solution of 14.4 g of 16-dimethylaminomethylene-3,3-(2,2-dimethylpropane-1,3-dioxy)-5(10),9(11)estradien-17-one in 220 ml of toluene is combined under ice water cooling dropwise with 85 ml of a 5% solution of methyllithium in diethyl ether. After the addition step, the mixture is agitated for 15 minutes at +5° to +10° C., excess reagent is decomposed by gently adding about 20 ml of water, the reaction solution is then poured into about 3 l of ice water, and extracted with methylene chloride. The crude product is chromatographed on neutral aluminum oxide with hexane/ethyl acetate. After crystallizing the main fraction from ethyl acetate, 13.0 g of 3,3-(2,2-dimethylpropane-1,3-dioxy)-6(E)-ethylidene-5(10),9(11)-estradien-17-one is obtained, mp 121°–123° C.

(c) Under ice water cooling, 4.3 ml of 30% hydrogen peroxide is added dropwise to a solution of 9.4 g of 3,3-(2,2-dimethylpropane-1,3-dioxy)-16(E)-ethylidene-5(10),9(11)-estradien-17-one in 43 ml of methylene chloride, 0.34 ml of hexachloroacetone, and 0.01 ml of pyridine, and then the mixture is stirred for 16 hours at 25° C. For working-up purposes, the reaction solution is diluted with about 100 ml of methylene chloride, washed in succession with 5% Na₂S₂O₃ solution and water, the methylene chloride phase is dried over Na₂SO₄, and concentrated. The resultant 5,10-epoxide mixture is chromatographed on Al₂O₃ (neutral, stage III) with hexane/ ethyl acetate, thus obtaining 4.7 g of 3,3-(2,2-dimethylpropane-1,3-dioxy)-5α,10α-epoxy-16(E)-ethylidene-9(11)-estren-17-one, mp 139°–141° C. (ethyl acetate/diisopropyl ether).

(d) At 0° to +5° C., a solution of 1.95 g of 3-(tetrahydropyran-2-yloxy)-1-propyne in 41 ml of absolute tetrahydrofuran (THF) is combined dropwise with 11.3 ml of a 15% solution of n-butyllithium in hexane. Thereafter a solution of 2.25 g of 3,3-(2,2-dimethylpropane-1,3-dioxy)-5α,10α-epoxy-16(E)-ethylidene-9(11)-estren-17-one is added dropwise thereto, and the mixture is stirred for 60 minutes at room temperature. To work up the mixture, it is poured into ice water and extracted with ethyl acetate. The crude product is crystallized from diisopropyl ether, thus obtaining 2.8 g of 3,3-(2,2-dimethylpropane-1,3-dioxy)-5α,10α-epoxy-16(E)-ethylidene-17α-[3-(tetrahydropyran-2-yloxy)-1-propynyl 9(11)-estren-17β-ol, mp 196°–198° C.

(e) At room temperature, 0.05 ml of methyl iodide is added and in succession a solution of 6.42 g of 4-bromodimethylaniline in 30 ml of absolute THF is added dropwise to a suspension of 604 mg of magnesium in 10 ml of absolute THF in such a way that the internal temperature does not rise above 45° C. After the magnesium is completely dissolved, the mixture is cooled to 0° C., 124 mg of CuCl (solid) is added, and the mixture is stirred for 15 minutes at 0° C. Then a solution of 3.5 g of 3,3β2,2-dimethylpropane-1,3-dioxy)-5α,10α-epoxy-16(E)-ethylidene-17α-[3-(tetrahydropyran-2-yloxy)-1-propynyl]-9(11)-estren-17β-ol in 25 ml of absolute THF is added dropwise and the mixture then stirred for 20 hours at 25° C. For working-up purposes, the mixture is poured into aqueous NH₃ solution and extracted with ethyl acetate. The crude product is chromatographed on Al₂O₃ with hexane/ethyl acetate. The oily main fraction (4.3 g) is utilized in the subsequent stage.

(f) A solution of 4.3 g of 11β-(4-dimethylaminophenyl)-3,3-(2,2-dimethylpropane-1,3-dioxy)-16(E)-ethylidene-17α-[3-(tetrahydropyran-2-yloxy)-1-propynyl]-9(10)-estrene-5α,17β-diol, obtained in (e), in 300 ml of-ethanol and 7 ml of triethylamine is hydrogenated after addition of 500 mg of Pd/BaSO₄ (10%) at room temperature and under normal pressure. After absorption of 140 ml of hydrogen, the reaction is terminated, the product filtered off from the catalyst, and concentrated. Yield: 4.3 g of 11β-(4-dimethylaminophenyl)-3,3-(2,2-dimethylpropane-1,3-dioxy)-16(E)-ethylidene-17α-[3-(tetrahydropyran-2-yloxy)prop-1(Z)-enyl-9(10)-estrene-5α,17β-diol as a colorless oil.

(g) A solution of 3.63 g of the product obtained in (f) in 17 ml of 70% aqueous acetic acid is agitated under argon for 20 hours at room temperature. The mixture is then poured ih ice water, a pH of about 10.5 is set by adding concentrated aqueous NH₃ solution, and the mixture is extracted with ethyl acetate. The crude product is chromatgraphed on silica gel with hexane/ethyl acetate. The main fraction is crystallized from hexane/ethanol, thus obtaining 1.3 g of 11β-(4-dimethylaminophenyl)-16(E)-ethylidene-17β-hydroxy-17α-(3-hydroxyprop-1(Z)-enyl)-4,9(10)-estradien-3-one, mp 127°–130° C. (the compound crystallizes with 1 mole of ethanol).

EXAMPLE 11

11β-(4-Dimethylaminophenyl)-17β-hydroxy-17α-(3-hydroxyprop-1(Z)-enyl)-4,9(10)-estradien-3-one (a)

11β-(4-Dimethylaminophenyl)-3,3-ethylenedioxy-17α-(3-hydroxyprop-1(Z)-enyl)-9-estrene-5α,17β-diol A solution of 500 mg of 11β-(4-dimethylaminophenyl)-3,3-ethylenedioxy-17α-(3-hydroxy-1-propynyl)-9-estrene-5α,17β-diol in 5 ml of ethanol is hydrogenated after addition of 5 mg of Lindlar catalyst (Pd/CaCO₃ [5%] with addition of Pb(OAcetyl)₂) for 16 hours at room temperature and under normal pressure. Hydrogen absorption was 22.7 ml. The reaction solution is suctioned off over "Celite", diatomaceous earth, washed with ethyl acetate, and concentrated to dryness under vacuum. The crude product is purified on 100 g of silica gel with a methylene chloride-acetone gradient (0°–20% acetone), thus isolating 420 mg of 11-(4-dimethylacminophenyl)-3,3-ethylene-dioxy-17-(3-hydroxyprop-1(Z)-enyl)-9-estrene-5,17 diol as a colorless foam. $[\alpha]_D^{25} = -13°$.

(b)

11β-(4-Dimethylaminophenyl)-17β-hydroxy-17α(3-hydroxyprop-1(Z)-enyl) 4,9(10)-estradien-3-one A solution of 255 mg of 11β-(4-dimethylaminphenyl)-3,3-ethylenedioxy-17α-(3-hydroxyprop-1(Z)-enyl)-9- estrene-5α,17β-diol in 4 ml of ethanol is stirred with 15 mg of pyridinium tosylate for 15 minutes at a bath temperature of 55° C. After adding a few drops of pyridine, the solvent is evaporated under vacuum. The residue is chromatographed on 50 g of silica gel with n-hexane/ethyl acetate, thus isolating 210 mg of 11β-(4-dimethylaminophenyl)-17βhydroxy-17α-(3-hydroxyprop-1(Z)-enyl)-4,9(10)-estradien-3-one as a solid foam.

EXAMPLE 12

17α-(3-Acetoxyprop-1(Z)-enyl)-11β-(4-dimethylaminphenyl)-17β-hydroxy-4,9(10)-estradien-3-one 1.1 g of 11β-(4-dimethylaminophenyl)-17β-hydroxy-17α-(3-hydroxyprop-1(Z)-enyl)-4,9(10)-estradien-3-one is agitated under a protective gas for 3 hours at room temperature in 20 ml of pyridine and 10 ml of acetic anhydride. The reaction mixture is worked up by stirring into an ice/water mixture and extraction with ethyl acetate. The organic phase is washed in succession with NaHCO₃ solution and water and dried over Na₂SO₄. After concentration, the product is chromatographed on silica gel with n-hexane/ethyl acetate, thus obtaining 1.15 g of 17α-(3-acetoxyprop-1(Z)-enyl)-11β-(4-dimethylaminophenyl)-17β-hydroxy-4,-9(10)-estradien-3-one as a lemon-yellow, solid foam.

$[\alpha]_D$ (CHCl₃) = +197°.

EXAMPLE 13

17β-Hydroxy-17α-(3-hydroxyprop-1(Z)-enyl)-11β-(4-trimethylsilylphenyl)-4,9(10)-estradien-3-one Preparation of p-Bromotrimethylsilylbenzene:

Under argon, 94.4 g of p-dibromobenzene is cooled to −20° C. in 400 ml of absolute ether. To the solution is added dropwise 255 ml of 15% butyllithium in hexane so that the temperature does not rise above −10° C. Then the mixture is agitated for one hour at room temperature. After a negative Gilman test (H. Gilman, J. Swiss, J. Amer. Chem. Soc. 62: 1847 [1940]), the mixture is again cooled to −20° C. and 46 ml of trimethylchlorosilane in 200 ml of absolute ether is added dropwise thereto so that the temperature does not exceed −10° C. After the addition step is finished, the mixture is stirred for 16 hours at room temperature and another hour under reflux. The thus-formed precipitate is suctioned off and thoroughly washed with ether. The resultant filtrate is concentrated and then distilled with a water-jet aspirator, thus producing 65.52 g of p-bromotrimethylsilylbenzene, bp (16 torr) 103°–110° C.

(a) Under argon, a solution of 45.84 g of p-bromotrimethylsilylbenzene in 50 ml of absolute tetrahydrofuran is added to a suspension of 4.86 g of magnesium and 0.1 ml of methyl iodide in 30 ml of absolute tetrahydrofuran in such a way that, after onset of reaction, a temperature of +45° C. is not exceeded. After the magnesium is completely dissolved, the mixture is cooled to −20° C., 2 g of copper chloride is added, and the mixture is stirred for 15 minutes. Then a solution of 19.49 g of 3,3-(2,2-dimethylpropane-1,3-dioxy)-5α,10α-epoxy-17α-[3-(tetrahydropyran-2-yloxy)prop-1-ynyl]-9(11)-estren-17β-ol in 130 ml of absolute tetrahydrfuran is added dropwise at −20° C. After this adding step is finished, the mixture is allowed to come to room temperature and is agitated for another 2 hours. For working-up purposes, the mixture is poured into 200 g of ice/20 ml of saturated ammonium chloride solution and extracted with ethyl acetate. The organic phases are washed neutral with water and dried over sodium sulfate. The concentrated residue is chromatographed on Al₂O₃ (III, neutral) with n-hexane/ethyl acetate, thus obtaining 21.8 g of 3,3-(2,2-dimethylpropane-1,3-dioxy)-17α-[3-(tetrahydropyran-2-yloxy)prop-1-ynyl]-11β-(4-trimethylsilylphenyl)-9(10)-estrene-5α-17β-diol as a colorless, solid foam.

(b) Under normal conditions, 2.2 g of the product obtained in (a) is hydrogenated in 50 ml of ethanol and 2.2 ml of triethylamine with the addition of 0.22 g of palladium/BaSO₄ (10%). After absorption of 74 ml of hydrogen, the reaction is terminated, the product is filtered off from the catalyst, concentrated, and the residue is chromatographed with n-hexane/ethyl acetate on Al₂O₃ (III, neutral). Yield: 1.62 g of 3,3-(2,2-dimethylpropane-1,3-dioxy)-17α-3-(tetrahydropyran-2-yloxy)prop-1(Z)-enyl]-11β-(4-trimethylsilylphenyl)-9(10)-estrene-5α,17β-diol as a colorless, solid foam.

¹H NMR (CDCl₃): 7.5–7.15 ppm (qu., 4H, arom. CH, $J_{AB}$=5 Hz) 5.8–5.5 (m, 2H, $$^1\text{H NMR (CDCl}_3\text{): } 7.5\text{–}7.15 \text{ ppm (qu., 4H, arom. CH, } J_{AB} = 5 \text{ Hz)}$$

$$5.8\text{–}5.5 \text{ (m, 2H, } -\underset{H}{C}=\underset{H}{C}-, J_{cis} = 12 \text{ Hz)}$$

$$0.31 \text{ (s, 9H, Si(CH}_3)_3)$$

$J_{cis}$=12 Hz) 0.31 (s, 9H, Si(CH₃)₃).

(c) 5.98 g of the product obtained in (b) is agitated in 50 ml of 70% acetic acid for 3 hours at 50° C. For working-up purposes, the mixture is stirred into 50 g of ice/50 ml of concentrated aqueous ammonia solution and extracted with ethyl acetate. The organic phases are washed neutral with water and dried over sodium sulfate. The concentrated crude product is chromatographed on silica gel with n-hexane/ethyl acetate, thus obtaining 3.08 g of 17β-hydroxy-17α-(3-hydroxyprop-1(Z)-enyl)-11β-(4-trimethylsilylphenyl)-4,9(10)-estradien-3-one as colorless crystals, mp 198°–201° C.

$[\alpha]_D$ (CH₃OH) = +189.3°.

EXAMPLE 14

17β-Hydroxy-17α-(3-hydroxyprop-1(Z)-enyl)-11β-phenyl-4,9(10)-estradien-3-one (a) Under argon, 15.7 g of bromobenzene in 70 ml of absolute tetrahydrofuran is added dropwise to a suspension of 2.43 g of magnesium and 0.015 ml of methyl iodide in 30 ml of absolute tetrahydrofuran in such a way that the internal temperature does not exceed +45° C. After complete dissolution of the magnesium, 0.54 g of copper chloride is added at +5° C., and stirring is continued for another 15 minutes. Subsequently a solution of 18.4 g of 3,3-(2,2-dimethylpropane-1,3-dioxy)-5α,10α-epoxy-17α-[3-(tetrahydropyran-2-yloxy)prop-1-ynyl]-9(11)-estren-17β-ol in 100 ml of absolute tetrahydrofuran is added dropwise thereto and the mixture is stirred for 16 hours at room temperature. Working-up is performed by pouring into a mixture of 20 g of ice/20 ml of saturated ammonium chloride solution, and extraction with ethyl acetate. The organic phases are washed neutral with water and dried over sodium sulfate. The concentrated residue is chromatographed on Al₂O₃ (III, neutral) with n-hexane/ethyl acetate, thus obtaining 21.1 g of 3,3-(2,2-dimethylpropane-1,3-dioxy)-11β-phenyl-17α-[3-(tetrahydropyran-2-yloxy)prop-1- ynyl]-9(10)-estrene-5α,17β-diol as a colorless, solid foam.

(b) Under normal conditions, 3 g of the compound obtained in (a) is hydrogenated in 150 ml of absolute ethanol and 3 ml of triethylamine with the addition of 0.3 g of palladium/BaSO₄ (10%). After absorption of 112 ml of hydrogen, the reaction is terminated, the product is filtered off from the catalyst and concentrated. The residue is chromatographed on Al₂O₃ (III, neutral) with n-hexane/ethyl acetate, thus obtaining 2.18 g of 3,3-(2,2-dimethylpropane-1,3-dioxy)-11β-phenyl-17α-[3-(tetrahydropyran-2-yloxy)prop-1(Z)-enyl]-9(10)-estrene-5α,17β-diol as a colorless, solid foam.

$^1$H NMR (CDCl₃): 7.13 ppm (s, 5H, arom. CH)

$J_{cis}$ = 11 Hz)

(c) 2.18 g of the compound obtained in (b) is dissolved in 50 ml of 70% acetic acid and stirred at room temperature for 24 hours. The mixture is worked up by stirring into 50 g of ice/50 ml of concentrated aqueous ammonia solution and extraction with ethyl acetate. After the organic phases have been washed neutral with water and dried over sodium sulfate, they are chromatographed, after concentration, on silica gel with n-hexane/20–50% ethyl acetate, thus producing 0.43 g of 17β-hydroxy-17α-(3-hydroxyprop-1(Z)-enyl)-11β-phenyl-4,9(10)-estradien-3-one, isolated as colorless crystals, mp 245°–247° C.

[α]$_D$ (CHCl₃) = +148.1°.

EXAMPLE 15

11β-(4-N-Formyl-N-methylaminophenyl)-17β-hydroxy-17α-(3-hydroxyprop-1(Z)-enyl)-4,9(10)-estradien-3-one Under argon, 3.15 g of the product obtained in 3(a) is dissolved in 60 ml of absolute tetrahydrofuran and, under exclusion of moisture, 0.9 ml of acetic acid-formic acid anhydride is added dropwise at a temperature of −20° C. After a reaction period of one hour at room temperature, the solution is stirred into 60 g of ice/5 ml of concentrated aqueous ammonia solution and extracted with ethyl acetate. The organic phases are washed neutral with water, dried over sodium sulfate, and concentrated. The resultant residue is stirred with 100 ml of 70% acetic acid for 3 hours at 50° C. The solution is then poured on 100 g of ice/100 ml of concentrated aqueous ammonia solution and extracted with methylene chloride. The organic phases are washed neutral with water and dried over sodium sulfate, concentrated, and the residue chromatographed on silica gel with methylene chloride/acetone, thus obtaining 1.84 g of 11β-(4-N-formyl-N-methylaminophenyl)-17β-hydroxy-17α-(3-hydroxyprop-1(Z)-enyl)-4,9(10)-estradien-3-one.

[α]$_D$ (CH₃OH) = +185.7°.

EXAMPLE 16

11β-(4-N-Acetyl-N-methylaminophenyl)-17β-hydroxy-17α-(3-hydroxyprop-1(Z)-enyl)-4,9(10)-estradien-3-one Under argon, 3.15 g of the product obtained in 3(a) is dissolved in 40 ml of absolute pyridine. At +5° C., 0.41 ml of acetyl chloride is added dropwise so that the temperature does not exceed +10° C. The mixture is stirred for one hour at +5° C., then the solution is allowed to flow into 80 g of ice/40 ml of concentrated hydrochloric acid and extracted with methylene chloride. The organic phases, dried over sodium sulfate, are concentrated and the resultant residue is stirred in 100 ml of 70% acetic acid for 3 hours at 50° C. The mixture is worked up by pouring on 100 g of ice/100 ml of concentrated aqueous ammonia solution and extraction with methylene chloride. The organic phases are washed neutral with water and dried over sodium sulfate. After concentration, the residue is chromatographed on silica gel with methylene chloride/20–50% acetone, thus obtaining 1.8 g of 11β-(4-N-acetyl-N-methylaminophenyl)-17β-hydroxy-17α-(3-hydroxyprop-1(Z)-enyl)-4,9(10)-estradien-3-one.

[α]$_D$ (CH₃OH) = +156.4°.

EXAMPLE 17

11β-(4-Formylaminophenyl)-17β-hydroxy-17α-(3-hydroxyprop-1(Z)-enyl)-4,9(10)-estradien-3-one 1.2 g of the product obtained in 4(b) is dissolved in 40 ml of absolute tetrahydrofuran under argon and combined under exclusion of moisture with 0.52 ml of acetic acid-formic acid anhydride at a temperature of −20° C. After a reaction time of 30 minutes, the solution is stirred for working-up purposes into 30 g of ice/5 ml of concentrated aqueous ammonia solution and extracted with ethyl acetate. After drying over sodium sulfate, the resultant crude product is dissolved, for saponification, in 50 ml of 70% acetic acid and stirred for 3 hours at 50° C. The mixture is poured, for working it up, on 50 g of ice/50 ml of concentrated aqueous ammonia solution and extracted with methylene chloride. After drying over sodium sulfate, the mixture is concentrated and the residue chromatographed on silica gel with methylene chloride/30–100% acetone, thus obtaining 0.62 g of 11β-(4-formylaminophenyl)-17β-hydroxy-17α-(3-hydroxyprop-1(Z)-enyl)-4,9(10)-estradien-3-one.

[α]$_D$ (CH₃OH) = +193.7°.

EXAMPLE 18

11β-(4-Acetylaminophenyl)-17β-hydroxy-17α-(3-hydroxyprop-1(Z)-enyl)-4,9(10)-estradien-3-one Under argon, 1.6 g of the product obtained in 4(b) is dissolved in 40 ml of absolute pyridine. At +5° C., 0.21 ml of acetyl chloride is added dropwise so that the temperature does not rise above +10° C. After agitation for 4 hours at room temperature, the solution is stirred into 50 g of ice/40 ml of concentrated hydrochloric acid and extracted with methylene chloride. After drying over sodium sulfate, the thus-obtained crude product is stirred for 3 hours at 50° C. with 70 ml of 70% acetic acid. The solution is worked up by pouring into 70 g of ice/70 ml of concentrated aqueous ammonia solution and extraction with methylene chloride. The organic phase is dried over sodium sulfate, concentrated, and the resultant residue is chromatographed on silica gel with methylene chloride/50–100% acetone, thus obtaining 0.97 g of 11β-(4-acetylaminophenyl)-17β-hydroxy-17α-(3-hydroxyprop-1(Z)-enyl)-4,9(10)-estradien-3-one.

[α]$_D$ (CH₃OH) = +196°.

EXAMPLE 19

11β-(4-Dimethylaminophenyl)-17aβ-hydroxy-17aα-(3-hydroxyprop-1(Z)-enyl)-D-homo-4,9,16-estratrien-3-one (a) A solution of 22.4 g of D-homo-4,9,16-estratriene-3,17a-dione in 225 ml of methylene chloride is combined in succession with 22.4 g of 2,2-dimethylpropane-1,3-diol, 11.2 ml of trimethyl orthoformate, and 20 mg of p-toluenesulfonic acid. The mixture is stirred for 2.5 hours at room temperature, diluted with 150 ml of methylene chloride, washed with saturated sodium bicarbonate solution, dried over sodium sulfate, and concentrated. The oily residue is chromatographed over $Al_2O_3$ (neutral, III) with hexane/ethyl acetate. After crystallization of the main fraction from diisopropyl ether, 19.1 g of 3,3-(2,2-dimethylpropane-1,3-dioxy)-D-homo-5(10),9(11),16-estratrien-17a-one is obtained, mp 154°–156° C.

(b) Under ice water cooling, 7.6 ml of 30% $H_2O_2$ is added dropwise to a solution of 19.1 g of 3,3-(2,2-dimethylpropane-1,3-dioxy)-D-homo-5(10),9(11),16-estratrien-17a-one in 75 ml of methylene chloride, 0.6 ml of hexachloroacetone, and 0.1 ml of pyridine. The mixture is stirred at room temperature for 16 hours, diluted with 100 ml of methylene chloride, washed with 5% $Na_2S_2O_3$ solution, and concentrated. The thus-obtained mixture of 5α,10α-epoxide and 5β,10β-epoxide is separated by chromatography on $Al_2O_3$ with hexane/ethyl acetate. Crystallization from ethyl acetate/diisopropyl ether yields 9.7 g of 3,3-(2,2-dimethylpropane-1,3-dioxy)-5α,10α-epoxy-D-homo-9(11),16-estradien-17a-one, mp 188°–191° C.

(c) At 0° C., 53 ml of n-butyllithium/n-hexane (1.6 mol/l) is added dropwise under a protective gas to a solution of 9.24 g of 3-(tetrahydropyran-2-yloxy)-1-propyne in 183 ml of absolute tetrahydrofuran; the mixture is stirred for 15 minutes. Then a solution of 9.1 g of 3,3-(2,2-dimethylpropane-1,3-dioxy)-5α,10α-epoxy-D-homo-9(11),16-estradien-17a-one in 183 ml of absolute tetrahydrofuran is added dropwise, and the reaction mixture is stirred for 3 hours at 0° C. The mixture is gently decomposed with ice/water and extracted with ethyl acetate for working it up. The organic phases are washed with water, dried over sodium sulfate, combined with activated carbon, suctioned through "Celite", and concentrated. Yield: 17.4 g of 3,3-(2,2-dimethylpropane-1,3-dioxy)-5α,10α-epoxy-17aβ-hydroxy-17aα-[3-(tetrahydropyran-2-yloxy)prop-1-ynyl]D-homo-9(11),16-estradiene as a yellowish oil which is used without further purification in the subsequent stage.

(d) A solution of 24.8 g of 4-bromo-N,N-dimethylaniline in 124 ml of absolute tetrahydrofuran is added dropwise to a suspension of 2.27 g of magnesium and 0.05 ml of methyl iodide in 42 ml of absolute tetrahydrofuran so that the temperature, after onset of reaction, does not exceed 45° C. The mixture is stirred for another hour to completely dissolve the magnesium, then it is cooled to 0° C., combined with 480 mg of copper(I) chloride, and stirred for another 15 minutes. Subsequently a solution of 17.4 g of the crude product obtained in (c) in 83 ml of absolute tetrahydrofuran is added dropwise, and the mixture agitated for another 5 hours at room temperature. In order to work it up, the reaction mixture is poured into ice water, decomposed with ethyl acetate, filtered over "Celite", and the filtrate extracted with ethyl acetate. The organic phases are washed neutral with water, dried over sodium sulfate, filtered, and concentrated. The residue is chromatographed on $Al_2O_3$ (neutral, III) with hexane/ethyl acetate, thus obtaining 10.8 g of 3,3-(2,2-dimethylpropane-1,3-dioxy)-11β-(4-dimethylaminophenyl)-17aα-[3-(tetrahydropyran-2-yloxy)prop-1-ynyl]-D-homo-9(10)-16-estradiene-5α,17aβ-diol as a light-yellow oil.

(e) Under normal conditions, 10.8 g of the product obtained in (d) is hydrogenated in 182 ml of tetrahydrofuran and 5.3 ml of pyridine with the addition of 1.1 g of palladium/$BaSO_4$ (10%). After absorption of 410 ml of hydrogen, the reaction is terminated, the hydrogenation mixture is suctioned off through "Celite" and concentrated. The thus-obtained crude product is then taken up in 55 ml of 70% acetic acid and stirred for one hour at 60° C. under a protective gas. After cooling, the reaction mixture, for working-up purposes, is poured on ice water, a pH of 10-11 is carefully set with concentrated aqueous ammonia solution, and the mixture is extracted with ethyl acetate. The ethyl acetate phases are washed neutral with water, dried over sodium sulfate, filtered, and concentrated. The residue yields, by chromatography on silica gel with hexane/ethyl acetate, 5.1 g of 11β-(4-dimethylaminophenyl)-17aβ-hydroxy-17aα-(3-hydroxyprop-1(Z)-enyl)-D-homo-4,9,16-estratrien-3-one as a lemon-yellow, solid foam.

UV ($CH_3OH$): λ(ε)=205 nm (36,800), 256 nm (17,400), 304 nm (21,500).

EXAMPLE 20

17β-Hydroxy-17α-(3-hydroxyprop-1(Z)-enyl)-11β-(4-methoxyphenyl)-4,9(10)-estradien-3-one (a) Under argon, a solution of 7.46 g (5 ml) of p-bromoanisole in 5 ml of absolute tetrahydrofuran is added dropwise to a suspension of 970 mg of magnesium and 0.01 ml of methyl iodide in 10 ml of absolute tetrahydrofuran in such a way that, after onset of reaction, a temperature of 45° C. is not exceeded. After complete dissolution of the magnesium, the mixture is cooled to 0° C. and 400 mg of copper(I) chloride is added. The mixture is stirred for 15 minutes at 0° C. and then a solution of 3.9 g of 3,3-(2,2-dimethylpropane-1,3-dioxy)-5α,10α-epoxy-17α-[3-(tetrahydropyran-2-yloxy)prop-1-ynyl]-9(11)-estren-17β-ol in 20 ml of absolute tetrahydrofuran is added dropwise thereto. After the addition step, the mixture is agitated overnight at room temperature. The reaction mixture is worked up by pouring into 40 g of ice/10 ml of concentrated ammonium chloride solution and extraction with ethyl acetate. The organic phases are washed with water and dried over sodium sulfate. Thereafter the mixture is filtered, concentrated, and the residue is chromatographed on $Al_2O_3$ (III, neutral) with n-hexane/ethyl acetate, thus obtaining 4.1 g of 3,3-(2,2-dimethylpropane-1,3-dioxy)-11β-(4-methoxyphenyl)-17α-[3-(tetrahydropyran-2-yloxy)prop-1-ynyl]-9(10)-estrene-5α,17β-diol as a colorless, solid foam.

(b) 4.1 g of the product obtained in (a) is hydrogenated under normal conditions in 50 ml of ethanol and 4 ml of pyridine in the presence of 400 mg of palladium/$BaSO_4$ (10%). After absorption of 150 ml of hydrogen, the reaction is terminated, the mixture filtered off from the catalyst, and the residue chromatographed on $Al_2O_3$ (III, neutral) with n-hexane/ethyl acetate, thus producing 3.6 g of 3,3-(2,2-dimethylpropane-1,3-dioxy)-11β-(4-methoxyphenyl)-17α-[3-(tetrahydropyran-2- yloxy)prop-1(Z)-enyl]-9(10)-estrene-5α,17β-diol as a colorless, solid foam.

| $^1$H NMR (CDCl$_3$): 90 MHz | δ = 7.05; 6.75 ppm (dd, 4H, arom. CH, J = 8 Hz) 5.8–5.5 (m, 2H, —CH=CH—, J$_{cis}$ = 12 Hz) 3.75 (s, 3H, —OCH$_3$) |
|---|---|

(c) Under a protective gas, 3.5 g of the product obtained in (b) is agitated in 50 ml of 70% acetic acid for 2 hours at 50° C. The mixture is worked up by stirring into 50 g of ice/50 ml of concentrated aqueous ammonia solution and extraction with methylene chloride. The organic phases are washed neutral with water, dried over sodium sulfate, filtered, and concentrated. Chromatography of the residue on silica gel with n-hexane/ethyl acetate yields 2.2 g of 17β-hydroxy-17α-(3-hydroxyprop-1(Z)-enyl)-11β-(4-methoxyphenyl)-4,9(10)-estradien-3-one as a light-yellow, solid foam.

$^1$H NMR (CDCl$_3$): δ=7.03; 6.75 ppm (dd, 4H, arom. CH, J=8 Hz) 5.8–5.6 (m, 2H, —CH=CH—, J$_{cis}$=12.5 Hz) 3.77 (s, 3H, —OCH$_3$).

[α]$_D$ (CHCl$_3$)= +178°.

EXAMPLE 21

17β-Hydroxy-17α-(3-hydroxyprop-1(Z)-enyl)-11β-(4-methylmercaptophenyl)-4,9(10)-estradien-3-one (a) Under argon, 4.06 g of 4-bromothioanisole in 10 ml of absolute tetrahydrofuran is added dropwise to a suspension of 486 mg of magnesium and 0.01 ml of methyl iodide in 10 ml of absolute tetrahydrofuran so that the temperature, after onset of reaction, does not exceed 45° C. After the magnesium is completely dissolved, the reaction mixture is cooled to 0° C., and 100 mg of copper(I) chloride is added. After another 15 minutes of agitation, a solution of 3.68 g of 3,3-(2,2-dimethylpropane-1,3-dioxy)-5α,10α-epoxy-17α-[3-(tetrahydropyran-2-yloxy)prop-1-ynyl]-9(11)-estren-17α-ol in 20 ml of absolute tetrahydrofuran is added dropwise thereto and the mixture is stirred overnight at room temperature. The mixture is worked up by pouring on 40 g of ice/40 ml of concentrated ammonium chloride solution and extraction with ethyl acetate. The organic phases are washed with water, dried over sodium sulfate, filtered, concentrated, and the residue is chromatographed on Al$_2$O$_3$ (III, neutral) with n-hexane/ethyl acetate, thus obtaining 3.41 g of 3,3-(2,2-dimethylpropane-1,3-dioxy)-11β-(4-methylmercaptophenyl)-17α-[3-(tetrahydropyran-2-yloxy)prop-1-ynyl]-9(10)-estrene-5α,17β-diol as a colorless, solid foam.

(b) 3.41 g of the product obtained in (a) is hydrogenated under normal conditions in 50 ml of ethanol and 4 ml of pyridine in the presence of 350 mg of palladium/BaSO$_4$ (10%). After absorption of 125 ml of hydrogen, the reaction is terminated, the product is filtered off from the catalyst, and the residue is chromatographed on Al$_2$O$_3$ (III, neutral) with n-hexane/ethyl acetate. Yield: 3.04 g of 3,3-(2,2-dimethylpropane-1,3-dioxy)-11β-(4-methylmercaptophenyl)-17α-[3-(tetrahydropyran-2-yloxy)prop-1(Z)-enyl]-9(10)-estrene-5α,17β-diol as a colorless, solid foam.

| $^1$H NMR (CDCl$_3$): 90 MHz | δ = 7.05 ppm (s, 4H, arom. CH) 5.75–5.5 (m, 2H, —CH=CH—, J$_{cis}$ = 12 Hz) |
|---|---|
| | 2.36 (s, 3H, —SCH$_3$) |

(c) Under a protective gap, 2.9 g of the product obtained in (b) is agitated in 40 ml of 70% acetic acid for 2 hours at 50° C. The mixture is worked up by pouring into 40 g of ice/40 ml of concentrated aqueous ammonia solution and extracted with methylene chloride. The organic phases are washed neutral with water, dried over sodium sulfate, filtered, and concentrated. The residue is chromatographed with n-hexane/ethyl acetate on silica gel, thus obtaining 1.58 g of 17β-hydroxy-17α-(3-hydroxyprop-1(Z)-enyl)-11β-(4-methylmercaptophenyl)-4,9(10)-estradien-3-one as a pale-yellow, solid foam.

$^1$H NMR (CDCl$_3$): δ=7.03 ppm (s, 4H, arom. CH) 5.8–5.5 (m, 2H, —CH=CH—, J$_{cis}$=12 Hz) 2.35 (s, 3H, —SCH$_3$) .

What is claimed is:

1. An 11β-arylestradiene of the formula wherein

R$^1$ is hydrogen, wherein R$^I$ and R$^{II}$ each independently is hydrogen, alkyl of 1–4 carbon atoms, or alkanoyl of 1–8 carbon atoms, or R$^I$ and R$^{II}$ together with the connecting N-atom form a 5- or 6-membered saturated ring, the remaining atoms all being C-atoms or one being another N-atom or an O or S atom, a pyrrole ring being optionally substituted by 1–4 methyl groups;

a corresponding N-oxide

—OR$^{III}$, wherein R$^{III}$ is hydrogen, methyl, ethyl, propyl, methoxyphenyl, allyl, or dimethylaminoethyl, —SR$^{IV}$, wherein R$^{IV}$ is hydrogen, methyl, ethyl, propyl, or dimethylaminoethyl, or —SiR$_3^V$, wherein R$^V$ is methyl, ethyl, propyl, butyl, or benzyl, R$^2$ is a hydrogen atom, a methyl group, or an ethyl group, R$^3$ is a hydrogen atom or an alkanoyl group of 1–8 carbon atoms, and $$-\overset{\diagdown}{\underset{|}{A}} \text{ means } -CH_2, \quad -\overset{\diagdown}{\underset{|}{CH_2}} -\overset{\diagdown}{\underset{|}{CH_2}}, \quad -\overset{\diagdown}{\underset{|}{CH}}\overset{R^4}{\underset{}{}} \overset{\diagdown}{\underset{|}{C}}=R^5,$$

$$-\overset{\diagdown}{\underset{\|}{CH}}\overset{\diagdown}{\underset{}{CH}}, \quad -\overset{\diagdown}{\underset{|}{CH}}\overset{\diagdown}{\underset{|}{CH_2}}, \quad \overset{\diagdown}{\underset{|}{CH_2}}\overset{\diagdown}{\underset{|}{CH_2}}, \quad \overset{\diagdown}{\underset{|}{CH_2}}\overset{\diagdown}{\underset{|}{CH}}\overset{R^6}{\underset{}{}},$$

$$\overset{\diagdown}{\underset{|}{C}}=R^7 \quad \overset{\diagdown}{\underset{\|}{CH}} \quad \overset{\diagdown}{\underset{|}{CH}} CH_2$$
$$\overset{\diagdown}{\underset{|}{CH_2}}, \quad \overset{\diagdown}{\underset{|}{CH_2}} \text{ or } \overset{\diagdown}{\underset{|}{CH_2}}$$

wherein $R^4$ and $R^6$ each mean alkyl of 1–4 carbon atoms in the α- or β-position, and $R^5$ and $R^7$ each mean $C_{1-4}$-alkylidene in the E- or Z-configuration, and the $C_{20}/C_{21}$-double bond has a Z- or E-configuration, or a pharmacologically acceptable acid addition salt thereof when the compound is basic.

2. 11β-(4-Dimethylaminophenyl)-17β-hydroxy-17α-(3-hydroxyprop-1(Z)-enyl)-4,9(10)-estradien-3-one, a compound according to claim 1.

3. 11β-(4-Dimethylaminophenyl)-17β-hydroxy-17α-(3-hydroxyprop-1(E)-enyl)-4,9(10)-estradien-3-one, a compound according to claim 1.

4. 17β-Hydroxy-17α-(3-hydroxyprop-1(Z)-enyl)-11β-(4-methylaminophenyl)-4,9(10)-estradien-3-one, a compound according to claim 1.

5. 11β-(4-Aminophenyl)-17β-hydroxy-17α-(3-hydroxyprop-1(Z)-enyl)-4,9(10)-estradien-3-one, a compound according to claim 1.

6. 11β-(4-Dimethylaminophenyl)-17β-hydroxy-17α-(3-hydroxyprop-1(Z)-enyl)-16β-methyl-4,9(10)-estradien-3-one, a compound according to claim 1.

7. 11β-(4-Dimethylaminophenyl)-17β-hydroxy-17α-(3-hydroxyprop-1(Z)-enyl)-16α-methyl-4,9(10)-estradien-3-one, a compound according to claim 1.

8. 17β-Hydroxy-17α-(3-hydroxyprop-1(Z)-enyl)-11β-[4-(piperidin-1-yl)phenyl]-4,9(10)-estradien-3-one, a compound according to claim 1.

9. 17β-Hydroxy-17α-(3-hydroxyprop-1(Z)-enyl)-11β-[4-(pyrrolidin-1-yl)phenyl]-4,9(10)-estradien-3-one, a compound according to claim 1.

10. 11β-[4-(2,5-Dimethylpyrrol-1-yl)phenyl]-17β-hydroxy-17α-(3-hydroxyprop-1(Z)-enyl)-4,9(10)-estradien-3-one, a compound according to claim 1.

11. 11β-(4-Dimethylaminophenyl)-16(E)-ethylidene-17β-hydroxy-17α-(3-hydroxprop-1(Z)-enyl)-4,9(10)-estradien-3-one, a compound according to claim 1.

12. 17α-(3-Acetoxyprop-1(Z)-enyl)-11β-(4-dimethylaminophenyl)-17β-hydroxy-4,9(10)-estradien-3-one, a compound according to claim 1.

13. 17β-Hydroxy-17α-(3-hydroxyprop-1(Z)-enyl)-11β-(4-trimethylsilylphenyl)-4,9(10)-estradien-3-one, a compound according to claim 1.

14. 17β-Hydroxy-17α-(3-hydroxyprop-1(Z)-enyl)-11β-phenyl-4,9(10)-estradien-3-one, a compound according to claim 1.

15. 11β-(4-N-Formyl-N-methylaminophenyl)-17β-hydroxy-17α-(3-hydroxyprop-1(Z)-enyl)-4,9(10)-estradien-3-one, a compound according to claim 1.

16. 11β-(4-N-Acetyl-N-methylaminophenyl)-17β-hydroxy-17α-(3-hydroxyprop-1(Z)-enyl) 4,9(10)-estradien-3-one, a compound according to claim 1.

17. 11β-(4-Formylaminophenyl)-17β-hydroxy-17α-(3-hydroxyprop-1(Z)-enyl)-4,9(10)-estradien-3-one, a compound according to claim 1.

18. 11β-(4-Acetylaminophenyl)-17β-hydroxy-17α-(3-hydroxyprop-1(Z)-enyl)-4,9(10)-estradien-3-one, a compound according to claim 1.

19. 11β-(4-Dimethylaminophenyl)-17aβ-hydroxy-17aα-(3-hydroxyprop-1(Z)-enyl)-D-homo-4,9,16-estratrien-3-one, a compound according to claim 1.

20. 17β-Hydroxy-17α-(3-hydroxyprop-1(Z)-enyl)-11β-(4-methoxyphenyl)-4,9(10)-estradien-3-one, a compound according to claim 1.

21. 17β-Hydroxy-17α-(3-hydroxyprop-1(Z)-enyl)-11β-(4-methylmercaptophenyl)-4,9(10)-estradien-3-one, a compound according to claim 1.

22. A process for the production of compounds of Formula I

[Structure of Formula (I): steroid with $R^1$-phenyl at 11β, $R^2$, OH, and CH=CH—CH$_2$OR$^3$ with B–A substituents]

wherein $R^1$, $R^2$, $R^3$ and $$\overset{\diagdown}{\underset{|}{B}}$$
$$-A$$

have the meanings given in claim 1 and the $C_{20}/C_{21}$-double bond has a Z-configuration, which comprises selectively hydrogenating the acetylenic triple bond in a compound of general Formula II

[Structure of Formula (II): steroid with $R^1$-phenyl at 11β, $R^2$, OH, C≡C—CH$_2$OR, ketal group with Z—O—O and OH]

wherein
$R^1$, $R^2$ and $$\overset{\diagdown}{\underset{|}{B}}$$
$$-A$$

have the meanings given in Formula I,

Z is an ethylene group or a 2,2-dimethyltrimethylene group and

R is a hydrogen atom or an organic group that can be readily split off in an acidic medium or by hydrogenolysis, in the presence of a deactivated noble metal catalyst, to form an intermediate compound of the Formula III wherein $R^1$, $R^2$ and have the meanings given in Formula I and the $C_{20}/C_{21}$-double bond has a Z-configuration, and treating the intermediate compound of Formula III, with acid to hydrolyze the 3-ketal and the blocking group R, and split off water to form the 4,9(10)-dien-3- one system.

23. A process according to claim 22, wherein the catalyst is palladium on barium sulfate in the presence of a tertiary amine.

24. A process according to claim 22, wherein the catalyst is palladium on calcium carbonate in the presence of $Pb(OAcetyl)_2$.

25. A process for the production of compounds of Formula I wherein $R^1$, $R^2$, $R^3$ and have the meanings given in claim 1 and the $C_{20}/C_{21}$-double bond has an E-configuration, which comprises selectively reducing the acetylenic triple bond in a compound of general Formula II to form an intermediate compound of the Formula III wherein $R^1$, $R^2$ and have the meanings given in Formula I and the $C_{20}/C_{21}$-double bond has an E-configuration, and treating the intermediate compound of Formula III, with acid to hydrolyze the 3-ketal and the blocking group R, and split off water to form the 4,9(10)-dien-3- one system.

26. A process according to claim 25, wherein lithium aluminum hydride is used as the reducing agent.

27. An intermediate compound of the Formula III wherein
$R^1$ is a hydrogen atom, with $R^I$ and $R^{II}$ meaning hydrogen, alkyl of 1–4 carbon atoms, or acyl of 1–8 carbon atoms, or $R^I$ and $R^{II}$ with inclusion of N meaning a 5- or 6-membered ring wherein, besides N, still another hetero atom, such as O, N, S can be contained in the ring, as well as the corresponding N-oxides and acid addition salts, or $R^I$ and $R^{II}$ with inclusion of N meaning a pyrrole ring optionally substituted by methyl,

—$OR^{III}$ with $R^{III}$ meaning hydrogen, methyl, ethyl, propyl, methoxyphenyl, allyl, or dimethylaminoethyl,

—$SR^{IV}$ with $R^{IV}$ meaning hydrogen, methyl, ethyl, propyl, or dimethylaminoethyl, and —$SiR_3^{V}$ with $R^{V}$ meaning methyl, ethyl, propyl, butyl, or benzyl, $R^2$ is hydrogen atom, a methyl group, or an ethyl group, and wherein $R^4$ and $R^6$ each mean alkyl of 1–4 carbon atoms in the α- or β-position, and $R^5$ and $R^7$ each mean an alkylidene group in the E- or Z-configuration, and the $C_{20}/C_{21}$-double bond has a Z- or E-configuration.

28. An intermediate compound according to claim 27 wherein the $C_{20}/C_{21}$-double bond has the Z-configuration.

29. An intermediate compound according to claim 27 wherein the $C_{20}/C_{21}$-double bond has the E-configuration.

30. An antigestational composition comprising an antigestationally effective amount of a compound according to claim 1 and a pharmaceutically acceptable carrier.

31. An antimineralocorticoid composition comprising an antimineralocorticoidally effective amount of a compound according to claim 1 and a pharmaceutically acceptable carrier.

32. A method for reducing mineralocorticoid activity in a patient which comprises administering an antimineralocorticoidally effective amount of a compound according to claim 1.

33. A method for inducing menses in a patient which comprises administering thereto a menses-inducing effective amount of a compound according to claim 1.

34. A method of inducing an abortion in a pregnant female comprising administering a compound of claim 1 to the female.

35. A method of simultaneously achieving an antimineralocorticoid effect and an antigestagenic effect in a patient comprising administering a compound of claim 1 to the patient.

36. A compound of claim 1 wherein $R^1$ is

37. A compound of claim 1 wherein $R^1$ is dimethylamino.

38. A compound of claim 1 wherein

39. A compound of claim 1 wherein or the 16α- or 16β-methylated counterparts.

40. A compound of claim 1 wherein $R^2$ is H.

* * * * *

UNITED STATES PATENT AND TRADEMARK OFFICE
CERTIFICATE OF CORRECTION

PATENT NO. : 4,609,651

DATED : September 2, 1986

INVENTOR(S) : RALPH ROHDE ET AL

It is certified that error appears in the above-identified patent and that said Letters Patent is hereby corrected as shown below:

Column 29, Diagram of lines 1-20 should read:

means

Signed and Sealed this

Twenty-fifth Day of November, 1986

*Attest:*

DONALD J. QUIGG

*Attesting Officer*     Commissioner of Patents and Trademarks